(12) United States Patent
Burnside et al.

(10) Patent No.: US 8,062,351 B2
(45) Date of Patent: *Nov. 22, 2011

(54) STENT-GRAFT WITH BIOABSORBABLE STRUCTURAL SUPPORT

(75) Inventors: Diane K. Burnside, Coon Rapids, MN (US); Jonathan S. Stinson, Plymouth, MN (US); Paul F. Chouinard, Roseville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/714,620

(22) Filed: Mar. 1, 2010

(65) Prior Publication Data

US 2010/0152833 A1    Jun. 17, 2010

Related U.S. Application Data

(60) Continuation of application No. 11/498,226, filed on Aug. 2, 2006, now Pat. No. 7,699,887, which is a continuation of application No. 10/674,726, filed on Sep. 30, 2003, now Pat. No. 7,108,716, which is a division of application No. 08/993,985, filed on Dec. 18, 1997, now Pat. No. 6,626,939.

(51) Int. Cl.
    *A61F 2/06* (2006.01)
(52) U.S. Cl. .................................................... 623/1.38
(58) Field of Classification Search ................ 623/1.22, 623/1.38, 1.53
    See application file for complete search history.

(56) References Cited

U.S. PATENT DOCUMENTS

| | | | | |
|---|---|---|---|---|
| 5,957,974 A | * | 9/1999 | Thompson et al. | 623/1.13 |
| 6,245,103 B1 | * | 6/2001 | Stinson | 623/1.22 |
| 6,626,939 B1 | * | 9/2003 | Burnside et al. | 623/1.38 |
| 7,108,716 B2 | * | 9/2006 | Burnside et al. | 623/1.38 |

* cited by examiner

*Primary Examiner* — Bruce E Snow
(74) *Attorney, Agent, or Firm* — Vidas, Arrett & Steinkraus, P.A.

(57) ABSTRACT

The invention relates to a stent-graft with a bioabsorbable structure and a permanent graft for luminal support and treatment of arterial fistulas, occlusive disease, and aneurysms. The bioabsorbable structure is formed from braided filaments of materials such as PLA, PLLA, PDLA, and PGA and the graft is formed from materials such as PET, ePTFE, PCU or PU.

8 Claims, 33 Drawing Sheets

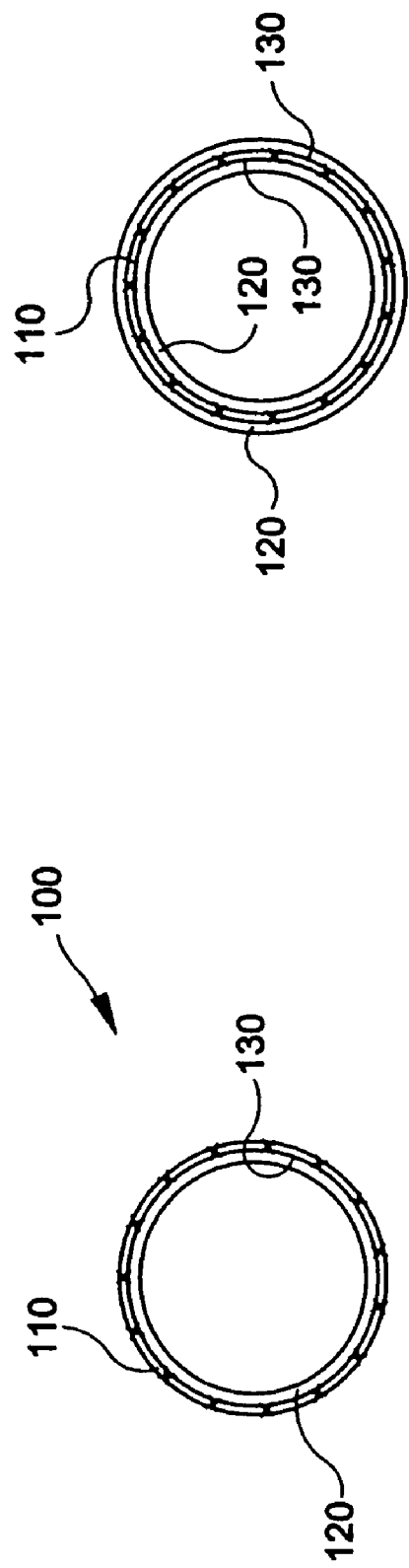

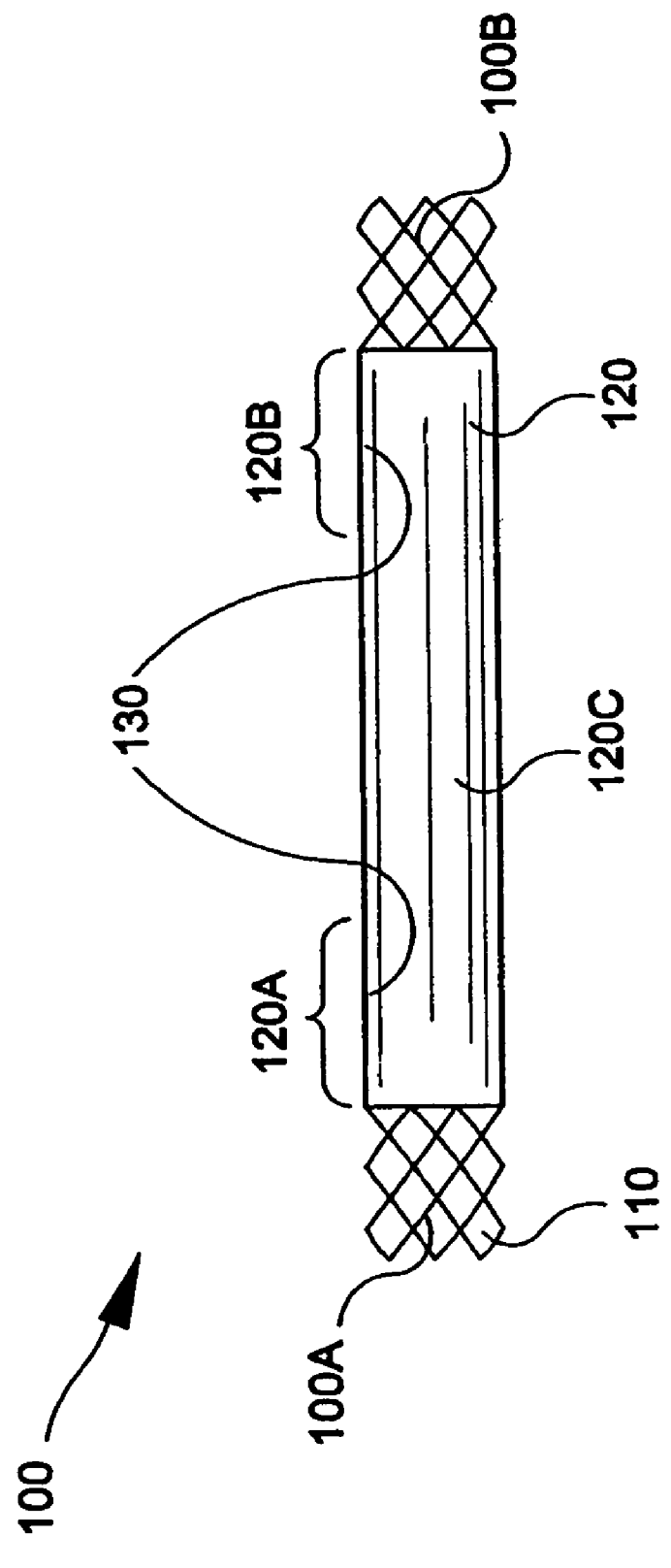

STENT-GRAFT WITH BIOABSORBABLE STRUCTURAL SUPPORT

CROSS-REFERENCE OF RELATED APPLICATIONS

This application is a continuation of U.S. patent application Ser. No. 11/498,226, filed Aug. 2, 2006, which is a continuation of U.S. patent application Ser. No. 10/674,726, filed Sep. 30, 2003, now U.S. Pat. No. 7,108,716, which is a divisional of U.S. application Ser. No. 08/993,985, filed Dec. 18, 1997, now U.S. Pat. No. 6,626,939, the contents of which are incorporated herein by reference.

BACKGROUND OF THE INVENTION

The present invention relates generally to implantable, radially expandable medical prostheses which are frequently referred to as stent-grafts. In particular, the present invention is a self-expanding stent-graft having a bioabsorbable structural component and a permanent graft component.

Self-expanding stents and methods for fabricating a stent are known and are, for example, shown in the U.S. Pat. Nos. 4,655,771; 4,954,126; 5,061,275; and in 5,645,559. Such devices are used within body vessels of humans for a variety of medical applications. Examples include intravascular stents for treating stenoses, stents for maintaining openings in the urinary, biliary, tracheobronchial, esophageal, renal tracts, and vena cava filters. A stent-graft is described in U.S. patent application Ser. No. 08/640,253, entitled "Cobalt-Chromium-Molybdenum Alloy Stent and Stent Graft," filed Apr. 30, 1996 (now U.S. Pat. No. 5,891,191).

A delivery device is used to deliver the stent-graft through vessels in the body to a treatment site. The flexible nature and reduced radius of the compressed stent-graft enables it to be delivered through relatively small and curved vessels.

All references cited herein, including the foregoing, are incorporated herein in their entireties for all purposes.

SUMMARY OF THE INVENTION

The present invention relates to a self-expanding stent-graft having a bioabsorbable structure such as a stent and a permanent graft bonded together with an adhesive. The implantable stent-graft may include a tubular, radially compressible, axially flexible and radially self-expandable structure made from bioabsorbable elongate filaments formed in a braid-like configuration and a graft made from materials such as polyethylene terephthalate (PET), expanded polytetrafluoroethylene (ePTFE), polycarbonate urethane (PCU) or polyurethane (PU). The graft may be adhered to a surface of the bioabsorbable structure or interwoven or braided into the bioabsorbable structure. The preferred graft of the stent-graft is made of braided, woven, or spray-cast PET, PCU, or PU fibers. The graft may also be made of film, sheet, or tube such as an ePTFE or PCU material. The graft is designed to remain permanently implanted in the body, however, small amounts of degradation may occur to the graft over time in the body environment.

The stent-graft generally assumes a substantially tubular form in an unloaded or expanded state when not subjected to external forces and is generally characterized by a longitudinal shortening upon radial expansion and a longitudinal lengthening upon radial contraction.

In a preferred embodiment, the bioabsorbable structure of the stent-graft assembly is a stent which substantially consists of a plurality of elongate polylactide bioabsorbable polymer filaments, helically wound and interwoven in a braided configuration to form a tube. The filaments may also be made of poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(anuno acids), or related copolymer materials.

Each bioabsorbable material has a characteristic degradation rate in the body. For example, PGA and polydioxanone are relatively fast-bioabsorbing materials (weeks to months) and PLA and polycaprolactone are relatively slow-bioabsorbing materials (months to years).

PLA, PLLA, PDLA and PGA have a tensile strength of from about 276 millions of Pascals (MPa) to about 827 MPa (40 thousands of pounds per square inch (ksi) to about 120 ksi); a tensile strength of 552 MPa (80 ksi) is typical; and a preferred tensile strength of from about 414 MPa (60 ksi) to about 827 MPa (120 ksi). Polydioxanone, polycaprolactone, and polygluconate include tensile strengths of from about 103 MPa (15 ksi) to about 414 MPa (60 ksi); a tensile strength of 241 MPa (35 ksi) is typical; and a preferred tensile strength of from about 172 MPa (25 ksi) to about 310 MPa (45 ksi).

PLA, PLLA, PDLA and PGA have a tensile modulus of from about 2758 MPa to 13790 MPa (400,000 pounds per square inch (psi) to about 2,000,000 psi); a tensile modulus of 6206 MPa (900,000 psi) is typical; and a preferred tensile modulus of from about 4827 MPa (700,000 psi) to about 8274 MPa (1,200,000 psi). Polydioxanone, polycaprolactone, and polygluconate have a tensile modulus of from about 1379 MPa (200,000 psi) to about 4827 MPa (700,000 psi); a tensile modulus of 3103 MPa (450,000 psi) is typical; and a preferred tensile modulus of from about 2413 MPa (350,000 psi) to about 3792 MPa (550,000 psi).

The preferred design for the bioabsorbable structure of the stent-graft includes 10-36 filaments braided into a tubular mesh configuration. Alternative designs could be made using more than 36 bioabsorbable filament strands. Stent-grafts are envisioned having as many as 500 filaments and which are made with braiders having sufficient carrier capacity.

Stents for arterial indications typically require high radial strength to resist elastic recoil after PTA dilation of the muscular arterial wall tissue. The radial strength of a stent-graft can be increased by increasing the number of filament strands in the design. Also the amount of open space in the stent mesh of the stent-grafts can be reduced by using more filament strands. It may be desirable to utilize stents with less open space if there is concern that the endoprosthesis may become occluded due to the ingrowth of tumorous tissue from cancer. A stent with little open space could be used to purposely seal off branch vessels from the main artery. Larger diameter stent-grafts require more filament strands in the braid to build the structural network over the larger surface area. Large stent-grafts would be needed for the aorta and for the trachea and esophagus. Also, large stent-grafts could be used in the airway and esophagus to seal off fistulas or to prevent or limit tissue ingrowth into the stent.

The present invention advantageously provides an improved scent-graft and a method for making and using such a stent-graft.

In sum, the invention relates to a stent-graft including a bioabsorbable structural support including a tubular body having open ends, a sidewall structure having openings therein, and an inside and an outside surface and a permanent graft having an inside and outside surface. One of the bioabsorbable structural support or the permanent graft cooperates with the other and provides a coextensive portion wherein at least a part of the coextensive portion has a length of the bioabsorbable structural support and a length of the permanent graft bonded or interbraided together. The coextensive portion may be part or all of the longitudinal length of the stent-graft. The stent-graft may be adjustable between a nominal state and a radially-reduced state. The tubular body may further include a plurality of bioabsorbable elements formed in a generally elongated shape which is generally radially compressible and self-expandable. The stent-graft may provide an initial radial force when implanted in a body lumen and the bioabsorbable structure portion bioabsorbs over time in-vivo with an eventual resulting decrease in radial force to the vessel wall, and the permanent graft portion substantially remains in the body lumen. The structural support and the permanent graft may be bonded by adhesive means and the adhesive means may be bioabsorbable. The adhesive means may occupy a proximal and a distal end portion but not a mid portion over the coextensive portion which the structural support and graft are coextensive one another. The bioabsorbable structural support may be made of at least one of poly (alpha-hydroxy acid), PGA, PLA, PLLA, PDLA, polycaprolactone, polydioxanone, polygluconate, polylactic acid-polyethylene oxide copolymers, modified cellulose, collagen, poly(hydroxybutyrate), polyanhydride, polyphosphoester, poly(amino acids), or combinations thereof and the graft may be made of at least one of PET, ePTFE, PCU, or PU. The elements may be substantially homogeneous in cross section and length. The graft may include a plurality of interwoven fibers, mono-filaments, multi-filaments, or yarns. The graft may be a film, sheet, or tube. The graft may form a composite wall with body tissue in the body lumen. The stent-graft may be permeated with body tissue and may provide structural support to a body lumen for less than about 3 years. The graft may be disposed on at least one of the inside and outside surface of the structural support. The graft and the filaments may be interbraided. The bioabsorbable structural support may be annealed.

The invention also relates to a stent-graft including a tubular, radially compressible and self-expandable braided and annealed structure having a first set of filaments each of which extends in a helix configuration along a center line of the stent and having a first common direction of winding. A second set of filaments each extend in a helix configuration along a center line of the stent and have a second common direction of winding. The second set of filaments cross the first set of filaments at an axially directed angle. Each filament includes bioabsorbable material and has a substantially solid and substantially uniform cross-section, a tensile strength of from about 276 MPa (40 ksi) to about 827 MPa (120 ksi), a tensile modulus of from about 2758 MPa (400,000 psi) to about 13790 MPa (2,000,000 psi), and an average diameter of from about 0.15 mm to about 0.6 mm. A permanent graft cooperates with at least a portion of the structure to form a stent-graft adapted to be disposed in a body lumen. The graft may conform with the structure. The first set and the second set may have the same number of filaments. Each of the first and second sets of filaments may include from about 5 filaments to about 18 filaments. The axially directed angle when in a free radially expanded state after being annealed but before being loaded on a delivery device may be between about 120 degrees and about 150 degrees.

The invention also relates to a method of making a stent-graft including braiding bioabsorbable filaments to form a tubular braid, the braid having a braid angle; disposing the braid on a mandrel; annealing the braid at a temperature between about the bioabsorbable filament glass transition temperature and about the melting point for a predetermined time to form an annealed stent; removing the stent from the mandrel, the stent having a filament crossing angle; providing a permanent graft; and adhering at least a portion of the graft to the annealed stent to form an assembly. The permanent graft may further comprise a braid angle and the method may further include prior to the step of adhering matching the braid angle of the permanent graft to about the stent filament crossing angle. The method may further include prior to the step of adhering, applying at least one of a thermoplastic adhesive, curable adhesive, and bioabsorbable polymer glue to the surface of the stent. The method may further include prior to the step of adhering, applying radial compression or axial elongation to the assembly to apply pressure over at least a portion of the stent and graft. The braid may be annealed at a temperature of from about 60° C. to about 180° C. for a period of time of from about 5 minutes to about 120 minutes or annealed at a temperature of from about 130° C. to about 150° C. for a period of time of from about 10 minutes to about 20 minutes.

The invention also relates to a method of making a stent-graft including braiding bioabsorbable elements to form a bioabsorbable tubular braid, the braid having a braid angle; providing a permanent graft film, sheet, or tube; disposing one of the permanent graft film, sheet, or tube or the bioabsorbable tubular braid on a mandrel; disposing the other of the permanent graft film, sheet, or tube or the bioabsorbable tubular braid over at least a portion of the other; adhering the permanent graft film, sheet, or tube to the braid to form a braid-graft; annealing the braid-graft at a temperature between about the bioabsorbable elements glass transition temperature and about the melting point for a predetermined time to form the stent-graft; and removing the stent-graft from the mandrel.

The graft film, sheet, or tube may include at least one of ePTFE and PCU and the bioabsorbable filament may include PLLA.

The invention also relates to a method of using a stent-graft including providing a tubular, radially self-expandable and radially compressible, axially flexible, braided and annealed structure comprising elongate bioabsorbable filaments. The filaments have a tensile strength of from about 276 MPa (40 ksi) to about 827 MPa (120 ksi), and a tensile modulus of from about 2758 MPa (400,000 psi) to about 13790 MPa (2,000,000 psi). Each filament has an average diameter of from about 0.15 mm to about 0.6 mm; providing adhesive means; and providing a permanent graft disposed and adhered with the adhesive means to at least a portion of the structure and forming a stent-graft assembly; deploying the stent-graft assembly into a body lumen at a treatment site; and allowing the stent-graft assembly to self-expand or expanding the stent-graft assembly in the body lumen. The bioabsorbable filaments may include PLLA, PDLA, PGA, or combinations thereof and the graft may include PET, ePTFE, PCU, or PU or combinations thereof.

The invention also relates to a method of using a stent-graft to regenerate a defective body vessel including disposing a stent-graft into a body vessel having a vessel wall with a defect in the vessel wall, and natural tissue generation ability. The stent-graft includes a bioabsorbable structure portion and a permanent graft portion and has an outside surface. The bioabsorbable structure portion provides temporary force to the body vessel and the permanent graft portion provides a permanent synthetic wall at the area of the defect in the body vessel and is receptive to growth of the natural tissue therein and thereabout; placing the stent-graft in the vicinity of the defect such that at least a portion of the stent-graft spans the defect in the vessel wall; providing contact between the outside surface of the stent-graft and the vessel wall whereby the stent-graft provides an initial radial force to the vessel wall; and allowing or promoting healing at or around the stent-graft, the bioabsorbable structure portion adapted to bioabsorb over time in-vivo with an eventual resulting decrease in radial force to the vessel wall, and the permanent graft portion adapted to substantially remain in the body lumen. The body vessel may be an artery. The permanent graft portion may be replaced over time by a composite wall including natural tissue and the permanent graft portion. The defect may be at least one of an aneurysm, fistula, occlusive disease, or recurrent occlusive disease. The defect may be substantially excluded from the body vessel by one of the stent-graft or the composite vessel wall.

Bioabsorbable resins such as PLLA, PDLA, and PGA are available from PURAC America, Inc. of Lincolnshire, Ill. Partially oriented yarns and flat yarns are commercially available from Wellman Inc. of Charlotte, N.C. The partially oriented yarns can be textured by Milliken, Inc. of Spartenburg, S.C. Silicone adhesive is commercially available from Applied Silicone of Ventura, Calif. The remaining materials discussed in the application are commercially available.

Still other objects and advantages of the present invention and methods of construction and use of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction and use, and its several details are capable of modification in various obvious respects, all without departing from the invention. Accordingly, the drawings and description are to be regarded as illustrative in nature, and not as restrictive.

BRIEF DESCRIPTION OF THE DRAWINGS

FIGS. 3a-3d are various embodiments of the stent-graft in an unconstrained, radially expanded state taken through 3-3 of FIG. 2 illustrating the graft disposed on the outside of the stent, interbraided or interwoven through the stent filaments, on the inside of the stent, and on both the inside and the outside stent, respectively.

FIG. 21 illustrates an alternative stent-graft with localized bonding of a bioabsorbable stent and a permanent graft;

DETAILED DESCRIPTION OF THE INVENTION

Figure 1:
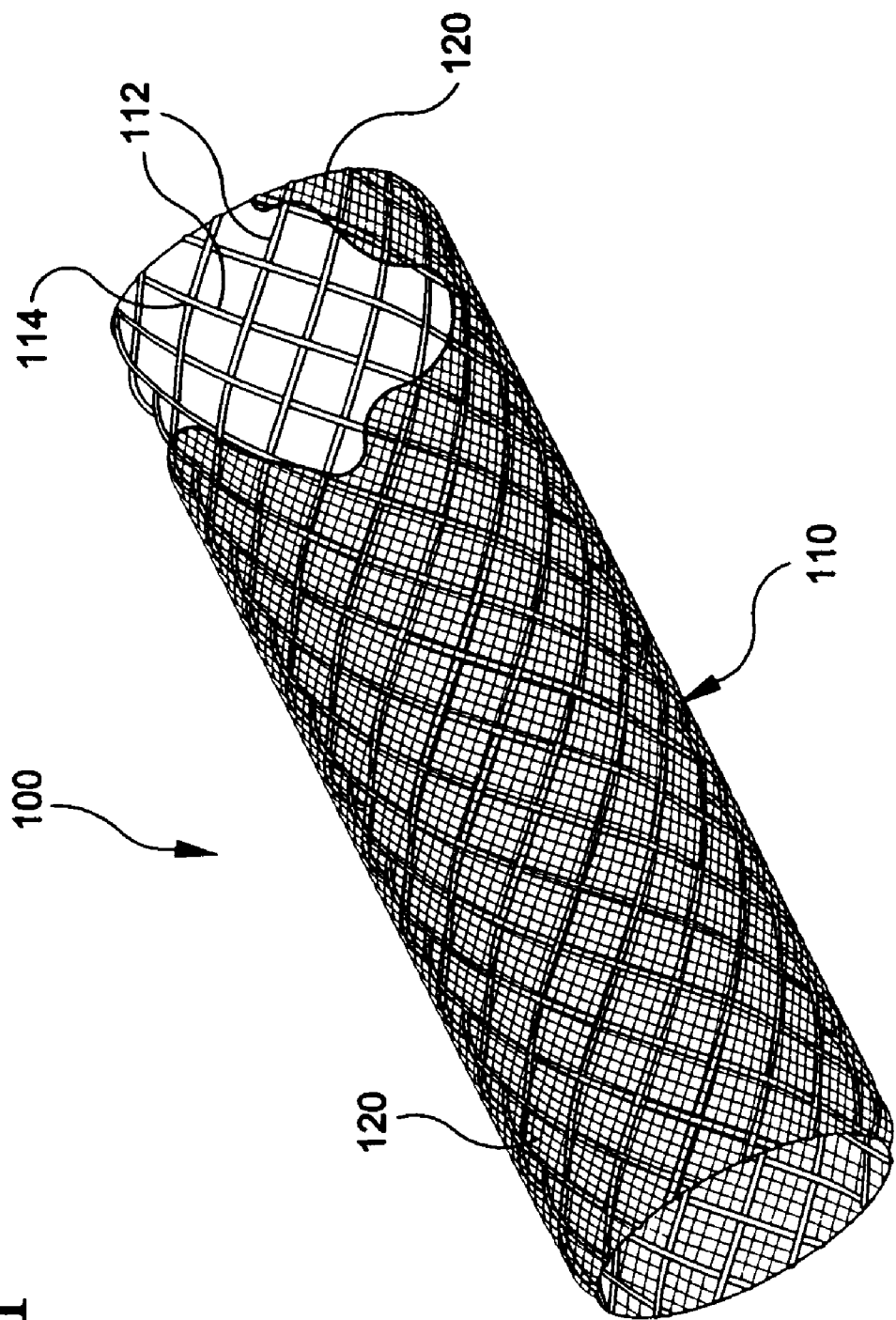
FIG. 1 is an isometric view of a stent-graft illustrating an exposed portion of the braided bioabsorbable filaments.
Figure 2:
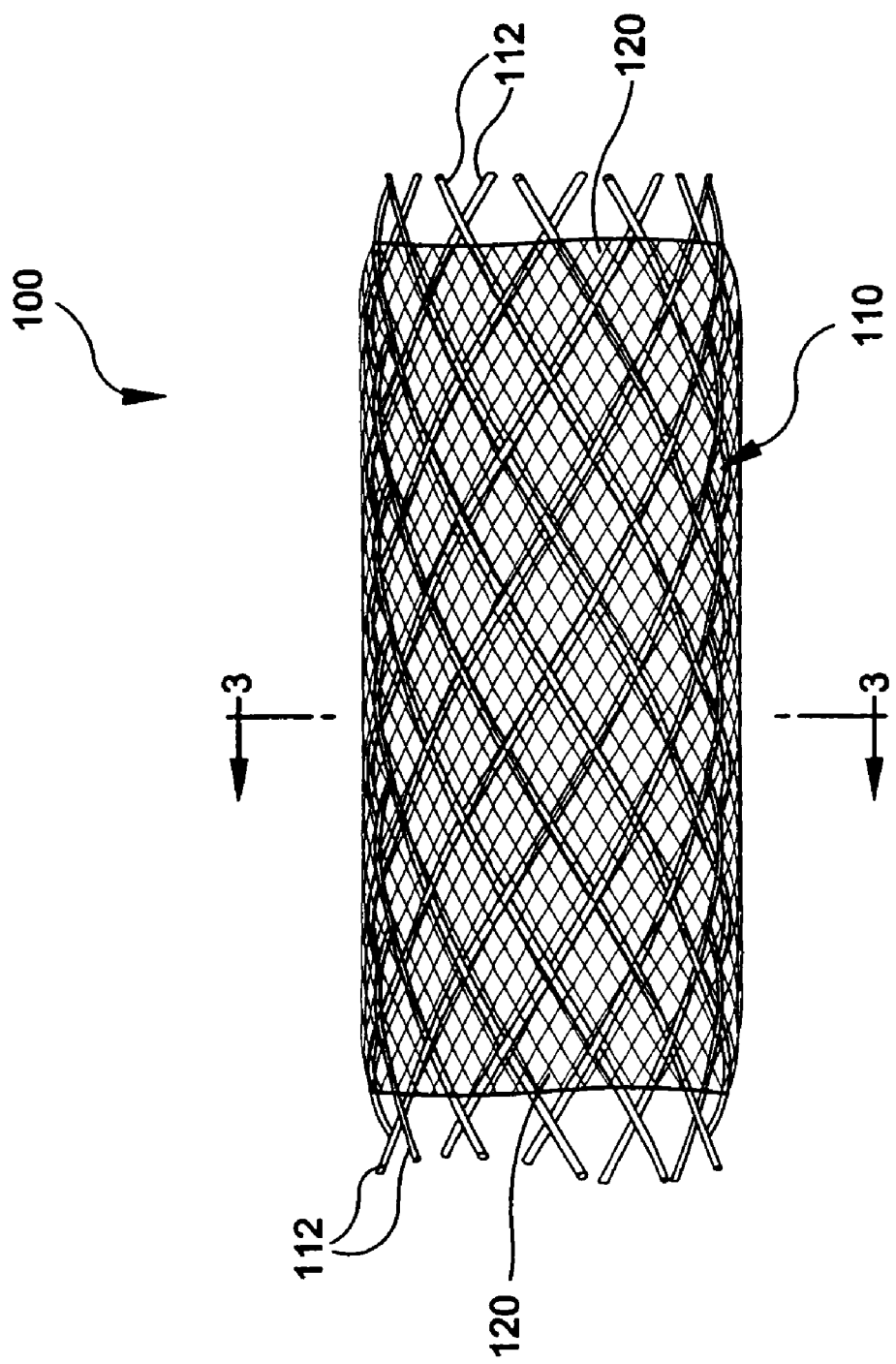
FIG. 2 is a side view of another embodiment of the stent-graft illustrating the graft disposed on a portion of the braided filaments.

A stent-graft 100 is shown generally in FIG. 1 with a permanent graft (graft) 120 covering substantially all of a bioabsorbable structural support (stent) 110 except an exposed portion which is shown uncovered for illustration purposes. An alternative embodiment of the stent-graft 100 is illustrated generally in FIG. 2 where the filaments 112 are exposed at each end and are not covered by the graft.

The support function of the bioabsorbable stent 110 portion of the stent-graft 100 is temporary while the function of the graft 120 is generally permanent. For example, after bracing the lumen open for a period of time necessary for tissue formation on and within the stent-graft 100, the stent 110 is gradually absorbed and vessel compliance and functional stresses are generally transferred to the new tissue. After implantation, the bioabsorbable stent 110 bioabsorbs over time and the generally compliant graft 120 and natural tissue remain in the vessel at the treatment site and form a composite vessel wall.

The stent 110 is formed from helically wound elongated filaments 112 and is preferably made of a non-toxic bioabsorbable polymer such as PGA, PLA, polycaprolactone, or polydioxanone, and the graft 120 is preferably made of braided or film PET, ePTFE, PCU, or PU.

The graft 120 is made of braided or interwoven material formed from fibers, strands, yarns, mono-filaments, or multi-filaments and is adhered with an adhesive to at least a portion of the stent 110. The graft 120 may also be formed from film, sheet, or tube. The especially preferred materials for the stent-graft 100 are PLLA for the bioabsorbable stent 110 and PET, PCU, or PU for the permanent graft 120.

Figure 3B:
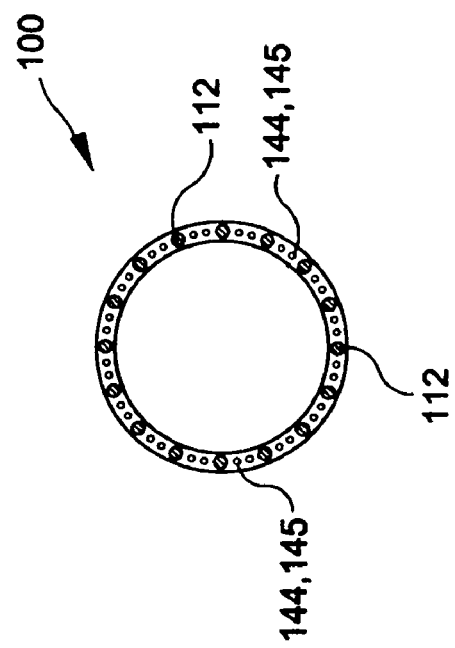
Figure 3A:
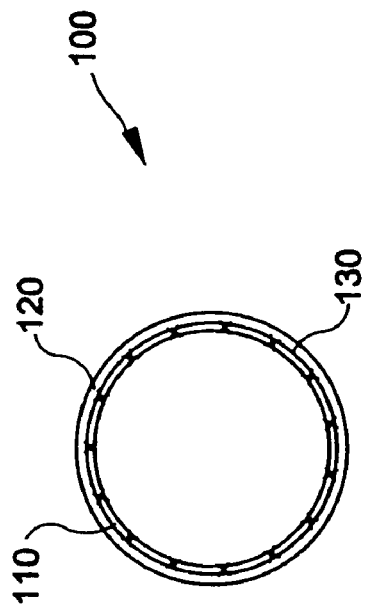
Figure 3E:
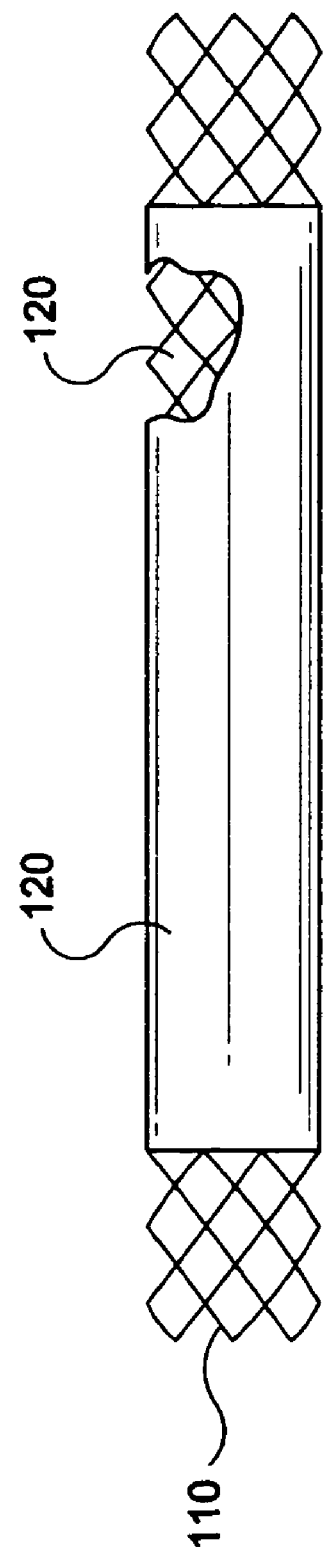
FIG. 3e is a side view of FIG. 3d illustrating the stent-graft.

Reference is made to FIGS. 3a-3e illustrating various embodiments of the stent-graft 100. The graft 120 is preferably disposed on the inside surface of the bioabsorbable stent 110 as shown in FIG. 3c. However, the graft 120 may be attached to the outside of the bioabsorbable stent 110 as shown in FIG. 3a or the graft elements 144, 145 may be interbraided or woven with the stent filaments 112 as, for example, shown in FIG. 3b. Alternatively, the graft 120 may be disposed on the inside surface and the outside surface of the bioabsorbable stent 110 as shown in FIG. 3d. FIG. 3e illustrates the stent-graft 100 with a cut-out showing both interior and exterior grafts 120.

The graft 120 and the stent 110 are adhered together at predetermined overlapping locations using an adhesive 130. The stent-graft 100 may be advantageously used for the treatment of arterial fistulas and aneurysms.

Additional detailed descriptions of the components of the stent-graft 100 and methods of making and use are described in further detail below.

A. The Bioabsorbable Structural Support

Figure 4:
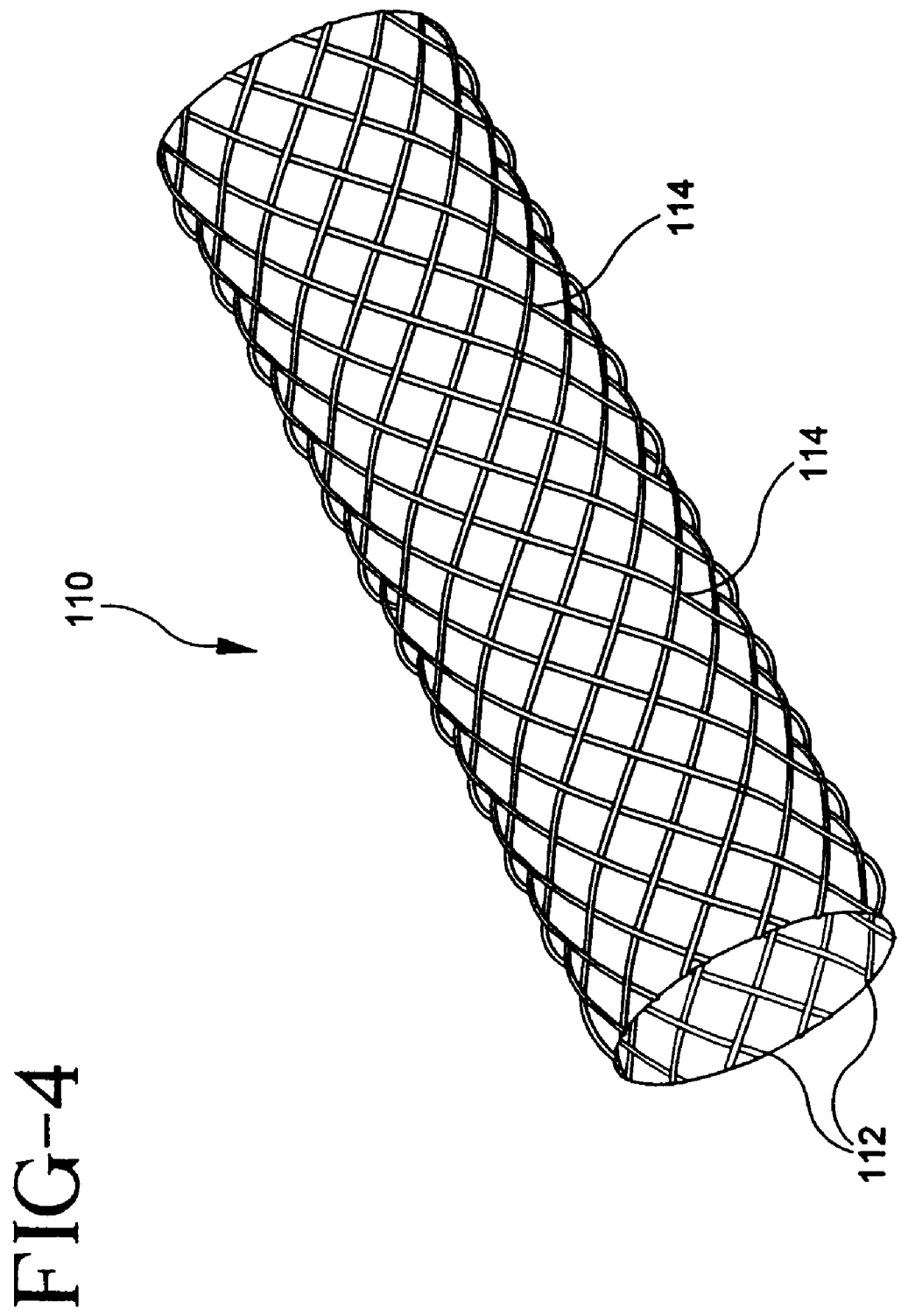
FIG. 4 is an isometric view of the bioabsorbable structure of the stent-graft.
Figure 5:
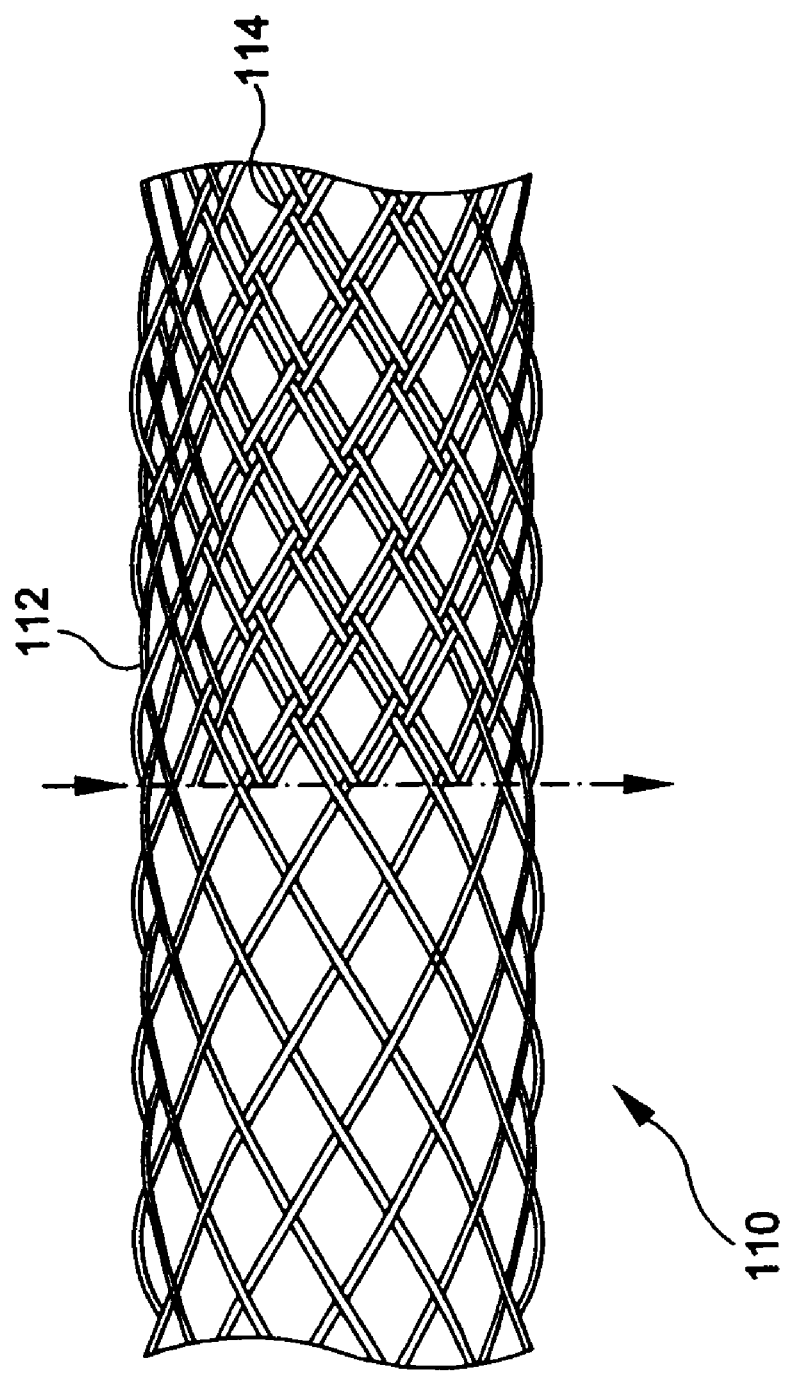
FIG. 5 is a partial longitudinal cross-sectional view of the bioabsorbable structure of the stent-graft.

Reference is made to FIGS. 4 and 5 showing the bioabsorbable structural support (stent) 110 of the stent-graft 100. Stent 110 is made of a plurality of individually rigid, but, flexible and elastic filaments 112, each of which extends in a helix configuration along a longitudinal center line of the body as a common axis. The filaments 112 define a radially self-expanding body. The sets of filaments 112 are interwoven in an over and under braided configuration intersecting at points such as 114 to form an open mesh or weave construction. The stent 110 maybe made with a first number of filaments 112 having a common direction of winding but axially displaced relative to each other, and crossing a second number of filaments 112 also axially displaced relative to each other but having an opposite direction of winding. FIG. 4 shows a stent 110 made of individual braided strands. FIG. 5 shows a stent 110 made of paired interbraided strands.

For reference and descriptive purposes, a braid becomes a stent 110 after annealing. Annealing of the braid relaxes the stresses in the filaments and sets the shape of the stent 110. The term "braid angle" refers to the included angle between interbraided filaments of the braid in the axial orientation prior to annealing and the term "filament crossing angle" refers to the included angle of the stent after annealing.

Figure 6:
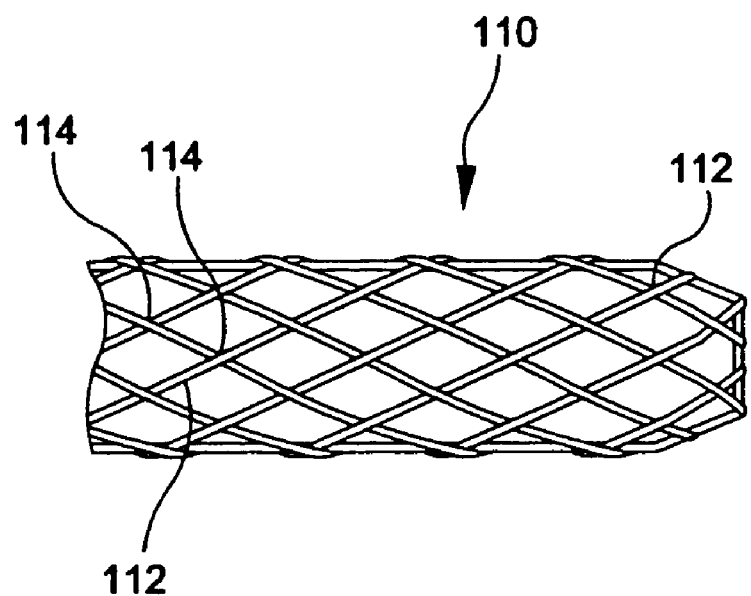
FIG. 6 is a side view of a second embodiment of the stent-graft.
Figure 7:
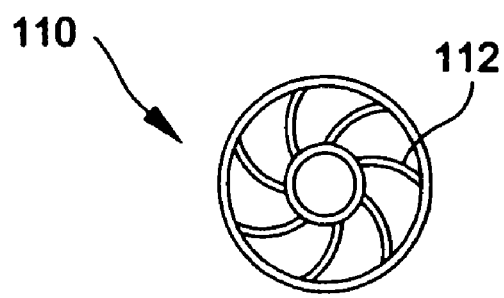
FIG. 7 is an end view of the stent-graft shown in FIG. 6.

The stent 110 may be made into various shapes, for example, as shown in FIGS. 6 and 7 where one end tapers and has a diameter which decreases in size. A tapered filament structure may be utilized as an intravascular filter or occlusion device.

Figure 8:
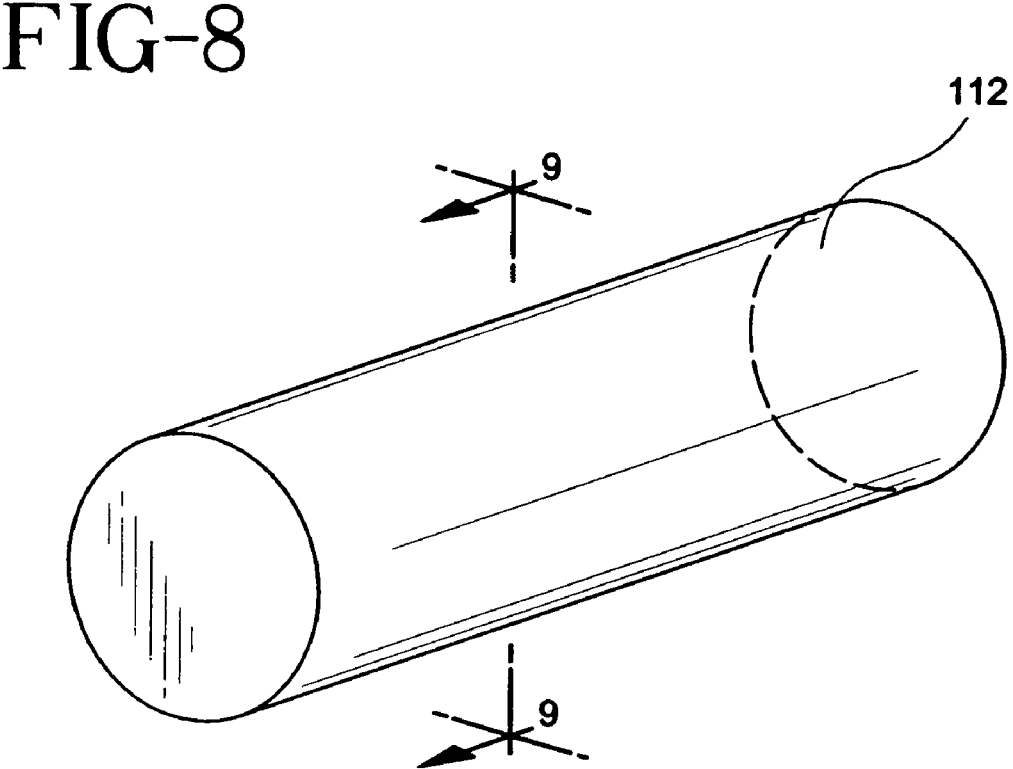
FIG. 8 is an isometric view of one of the filaments of the bioabsorbable structure.
Figure 9:
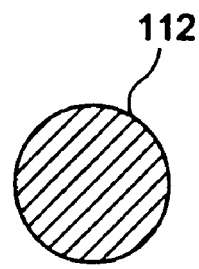
FIG. 9 is a cross-sectional view of one of the filaments of a bioabsorbable structure.

Reference is made to FIG. 8 which shows a portion of a typical filament 112 which makes up a stent 110. Stent 110 is shown in its expanded state when subject to no external loads or stresses. The filaments 112 are resilient, permitting the radial compression of stent 110 into a reduced-radius, extended-length configuration suitable for delivery transluminally to the desired treatment site. FIG. 9 illustrates a cross-sectional view of one embodiment of the bioabsorbable filaments 112. As shown, the filaments 112 are substantially homogeneous in cross section.

As described in greater detail below, at least one and preferably all filaments 112 include one or more commercially available grades of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly (amino acids), poly(alpha-hydroxy acid) or related copolymers materials.

A bioabsorbable stent is disclosed in U.S. patent application entitled "Bioabsorbable Self-Expanding Stent", Ser. No. 08/904,467, filed Aug. 1, 1997 (now U.S. Pat. No. 6,245,103). Another bioabsorbable stent is disclosed in U.S. patent application entitled "Bioabsorbable Implantable Endoprosthesis With Reservoir And Method Of Using Same," Ser. No. 08/905,806, filed Aug. 1, 1997 (now U.S. Pat. No. 5,980,564).

A stent 110 may be made by braiding between 10-36 independent strands of 0.15-0.60 mm diameter bioabsorbable polymeric filament 112 interwoven into helical shape strands on a round bar mandrel of 3-30 mm diameter. One-half of the number of helical strands are wound clockwise and one-half are wound counterclockwise such that each clockwise helical strand is adjacent and interbraided with a counterclockwise strand. The tubular braid is made with strand braid angle of about 120-150 degrees and a pitch angle (angle between a filament and transverse axis of the stent) of about 15-30 degrees while on the braid bar mandrel.

The braid is slid off of the braid bar and onto a 0.2-10 mm smaller diameter annealing bar or tube mandrel. Each end of the braid is pulled or compressed to cause axial extension or compression of the braid on the anneal mandrel, or left free. Each end of the braid is secured on each end of the anneal mandrel to fix the preset axial position of the braid, or left free. The braid is annealed on the anneal mandrel at a temperature between the glass-transition temperature and melting temperature of the bioabsorbable polymer for about 5-120 minutes in air, vacuum, or an inert atmosphere. The stent 110 is cooled on the anneal mandrel to about room temperature, slid off of the anneal mandrel, and cut to a desired length.

Figure 10A:
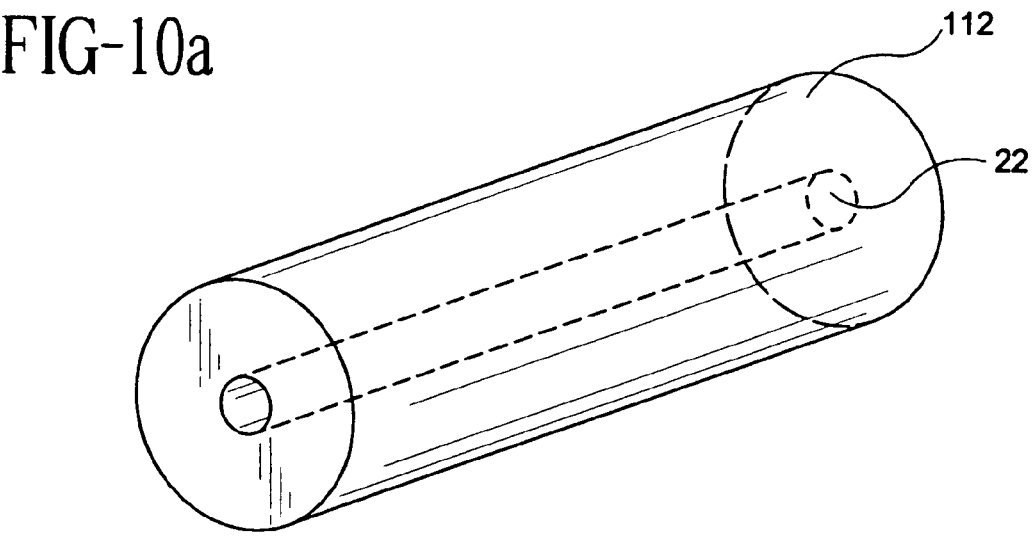
FIGS. 10a-10f are side views of embodiments of filaments having reservoir portions.
Figure 10B:
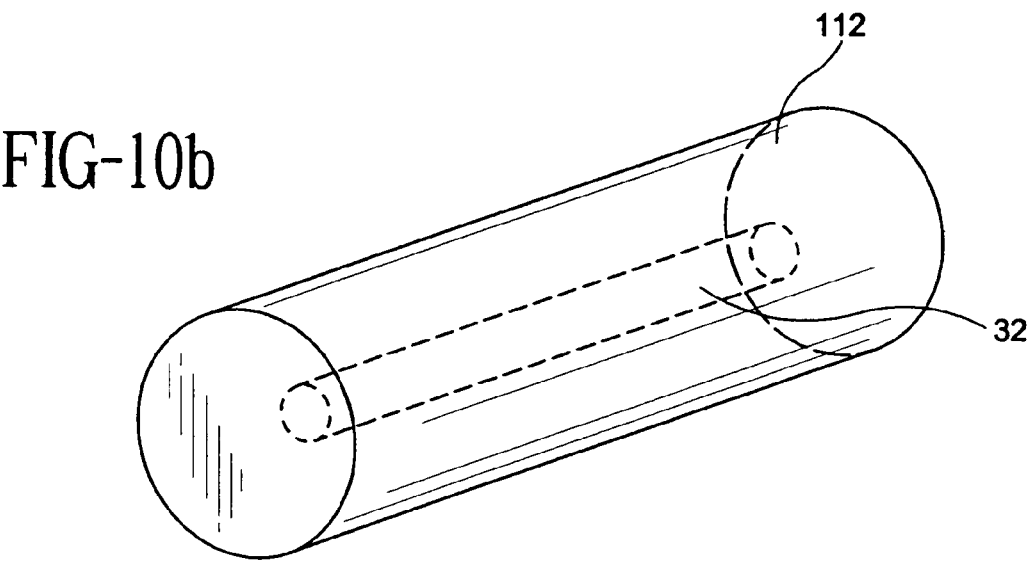
Figure 10C:
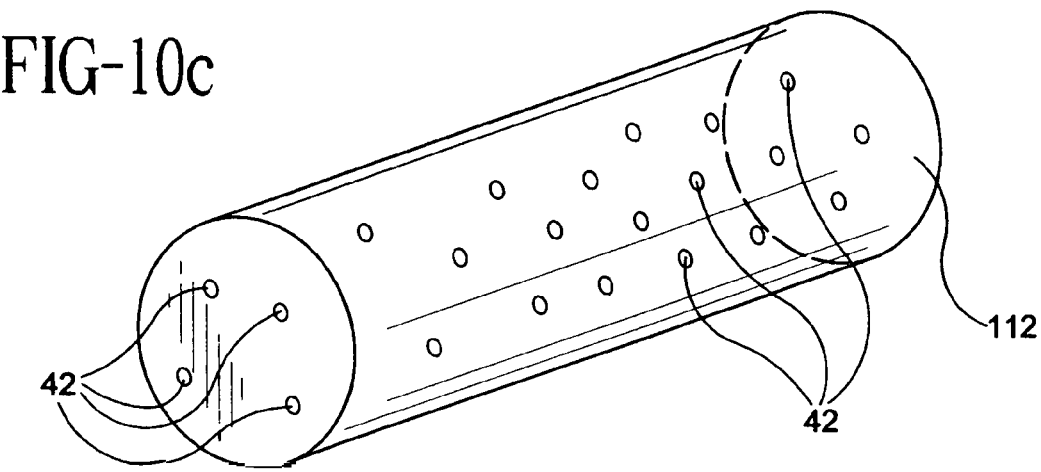
Figure 10D:
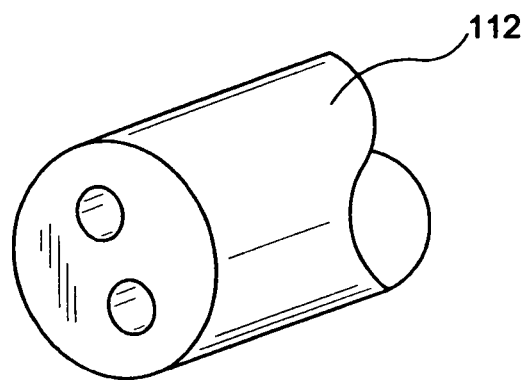
Figure 10E:
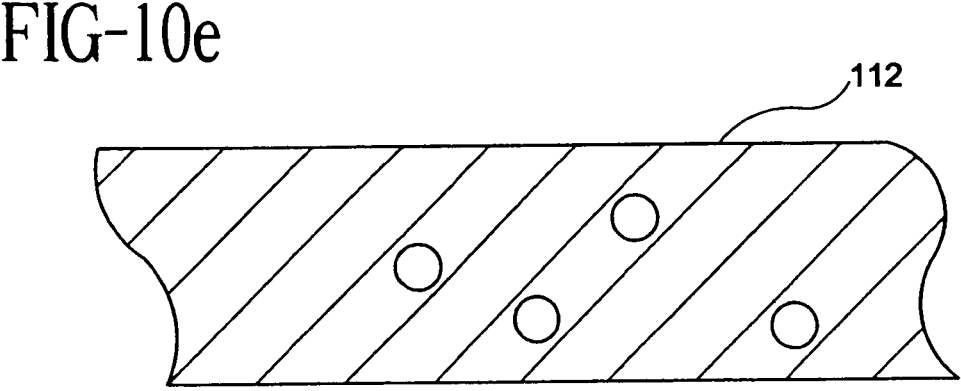
Figure 10F:
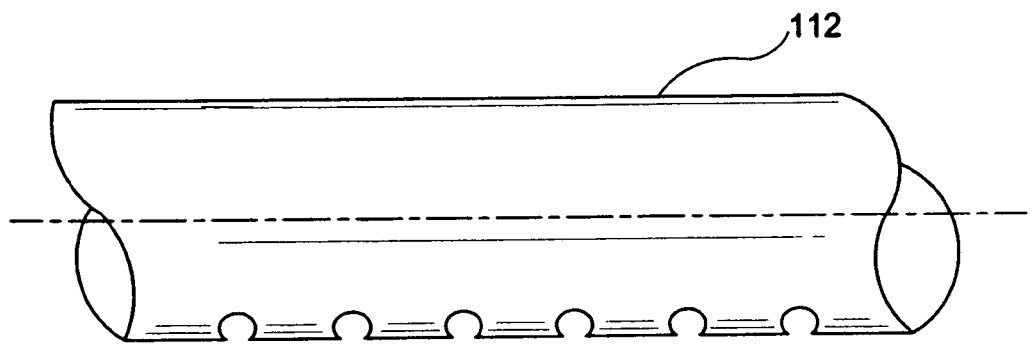

In addition to substantially solid and homogenous filaments 112, other embodiments of filaments 112 as shown in FIGS. 10a-10f and having one or more reservoir portions including hollow 22, cavity 32, porous 42 portions, or combinations thereof can be used. The term "reservoir" is referred to as a volume of space internal to the filament outer surface where polymer degradation by-products accumulate. The reservoir may include both internal and external passages, with the external passages opening through an outside wall or end of the filament 112. FIG. 10a illustrates a hollow filament 112 with a center core; FIG. 10b illustrates a filament 112 having at least one cavity with sealed ends; FIG. 10c illustrates a filament 112 having at least one pore (internal or external porosity, or both); FIG. 10d illustrates a multi-lumen filament 112 with a plurality of hollow portions; FIG. 10e illustrates a cross-section of a filament 112 having a plurality of internal pores; FIG. 10f illustrates a filament 112 having a plurality of surface pores. The external pores may connect with internal pores, cavities, or hollow portions. The reservoir portions have a size greater than about 1 micron and have a volume percentage greater than about 10%.

Although degradation occurs throughout the filament 112, the rate of degradation is generally higher at locations having a lower pH as acidic environments catalyze degradation. By-products from degradation such as lactic acid or glycolic acid are stored or accumulate in the reservoir portions which accelerate degradation of the inner surfaces.

Table I describes various preferred reservoir embodiments of filament 112.

TABLE I

| Type of Reservoir: | % Volume Solid | % Volume Hollow or Cavity | Hollow or Cavity Features Dimensions |
|---|---|---|---|
| axial core (one lumen tubing) | 65-90 | 10-35 | Ø < 50% of O.D. x length of filament strand |
| multi-lumen filament (two or more lumens) | 50-90 | 10-40 | Ø < 50% of O.D./# of lumens, length of filament strand |
| internal porosity | 70-90 | 10-30 | 1-20 microns |
| external porosity (surface oriented) | 80-90 | 10-20 | 1-20 microns |

The degradation by-products in the reservoir portions may have an average pH level which decreases over time in vivo. The average pH level in the reservoir may be between about 3 and 7. The endoprosthesis may substantially degrade in vivo in less than 3 years. The filaments may comprise PLLA, PDLA, or combinations thereof and substantially degrade in vivo in from about 1 year to about 2 years. The filaments may comprise polylactide, polyglycolide, or combinations thereof and substantially degrade in vivo in from about 3 months to about 1 year. The filaments may comprise polyglycolide, polygluconate, polydioxanone, or combinations thereof and substantially degrade in vivo in from about 1 week to about 3 months.

The filaments 112 may have an outer surface containing a multitude of empty pores which have an average depth of at least about 0.5 micron. The elongate filament 112 prior to implantation may contain at least one empty internal cavity which does not open to the filament 112 outer surface. The average cavity cross-sectional area is from about 2 to about 40 percent of the average filament 112 cross-sectional area.

Tables II and III show various embodiments of the bioabsorbable stent 110 of the stent-graft 100.

TABLE II

| # of Filament Strands in Stent | Brand Mandrel Diameter, mm | Braid Angle, Degrees | PLLA Diameter mm | PDLA Diameter, mm | PLLA/PDLA Diameter, mm | PGA Diameter, mm |
|---|---|---|---|---|---|---|
| 10 | 3-6 | 120-150 | .15-.25 | .15-.25 | .15-.25 | .20-.30 |
| 10 | 3-6 | 120-150 | .20-.30 | .20-.30 | .20-.30 | .25-.35 |
| 12 | 3-8 | 120-150 | .20-.30 | .20-.30 | .20-.30 | .25-.35 |
| 12 | 3-8 | 120-150 | .35-.45 | .35-.45 | .35-.45 | .40-.50 |
| 15 | 6-10 | 120-150 | .30-.40 | .30-.40 | .30-.40 | .35-.45 |
| 15 | 6-10 | 120-150 | .35-.45 | .35-.45 | .35-.45 | :40-.50 |
| 18 | 7-12 | 120-150 | .35-.45 | .35-.45 | .35-.45 | .40-.50 |
| 18 | 7-12 | 120-150 | .40-.50 | .40-.50 | .40-.50 | .45-.55 |
| 20 | 3-9 | 120-150 | .20-.30 | .20-.30 | .20-.30 | .25-.35 |
| 24 | 8-12 | 120-150 | .20-.30 | .20-.30 | .20-.30 | .25-.35 |
| 24 | 9-14 | 120-150 | .25-.35 | .25-.35 | .25-.35 | .30-.40 |
| 24 | 12-18 | 120-150 | .30-.40 | .30-.40 | .30-.40 | .35-.45 |
| 30 | 16-26 | 120-150 | .30-.40 | .30-.40 | .30-.40 | .35-.45 |
| 36 | 20-30 | 120-150 | .35-.45 | .35-.45 | .35-.45 | .40-.50 |
| 24 | 14-20 | 120-150 | .35-.45 | .35-.45 | .35-.45 | .40-.50 |

TABLE III

| # of Filament Strands in Braid | Braid Mandrel Diameter, mm | Braid Angle, Degrees | PGA/PLLA Diameter, mm | PGA/polycaprolactone diameter, mm | Polydioxanone diameter, mm | PGA/trimethylene carbonate diameter, mm |
|---|---|---|---|---|---|---|
| 10 | 3-6 | 120-150 | .20-.30 | .22-.32 | .25-.35 | .22-.32 |
| 10 | 3-6 | 120-150 | .25-.35 | .27-.37 | .30-.40 | .27-.37 |
| 12 | 3-8 | 120-150 | .25-.35 | .27-.37 | .30-.40 | .27-.37 |
| 12 | 3-8 | 120-150 | .40-.50 | .42-.52 | .45-.55 | .42-.52 |
| 15 | 6-10 | 120-150 | .35-.45 | .37-.47 | .40-.50 | .37-.47 |
| 15 | 6-10 | 120-150 | .40-.50 | .42-.52 | .45-.55 | .42-.52 |
| 18 | 7-12 | 120-150 | .40-.50 | .42-.52 | .45-.55 | .42-.52 |
| 18 | 7-12 | 120-150 | .45-.55 | .47-.57 | .50-.60 | .47-.57 |
| 20 | 3-9 | 120-150 | .25-.35 | .27-.37 | .30-.40 | .27-.37 |
| 24 | 8-12 | 120-150 | .25-.35 | .27-.37 | .30-.40 | .27-.37 |
| 24 | 9-14 | 120-150 | .30-.40 | .32-.42 | .35-.45 | .32-.42 |
| 24 | 12-18 | 120-150 | .35-.45 | .37-.47 | .40-.50 | .37-.47 |
| 30 | 16-26 | 120-150 | .35-.45 | .37-.47 | .40-.50 | .37-.47 |
| 36 | 20-30 | 120-150 | .40-.50 | .42-.52 | .45-.55 | .42-.52 |
| 24 | 14-20 | 120-150 | .40-.50 | .42-.52 | .45-.55 | .42-.52 |

A separately manufactured and permanent graft 120 is disposed on and adhered to a portion of the stent 110 with an adhesive to form the stent-graft 100 and is discussed in further detail below.

B. The Permanent Graft

The permanent graft 120 generally radially expands and contracts with the bioabsorbable stent 110. Vascular grafts are shown, for example, in U.S. Pat. No. 5,116,360.

Figure 11:
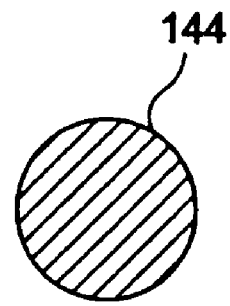
FIG. 11 is a cross-sectional view of a mono-filament strand of a permanent graft.
Figure 12:
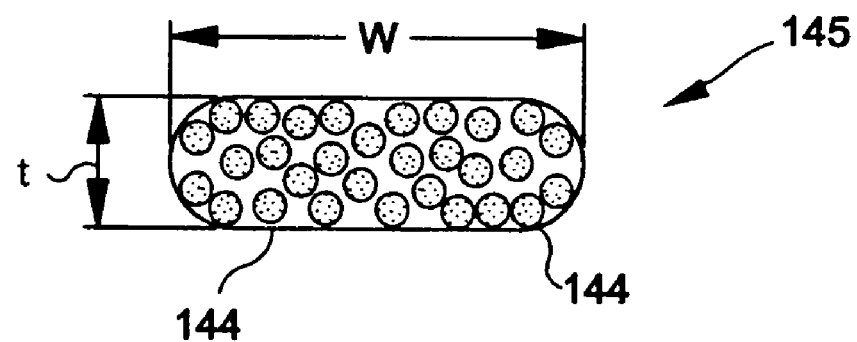
FIG. 12 is a cross-sectional view of a multi-filament yarn used in forming a permanent graft.
Figure 13:
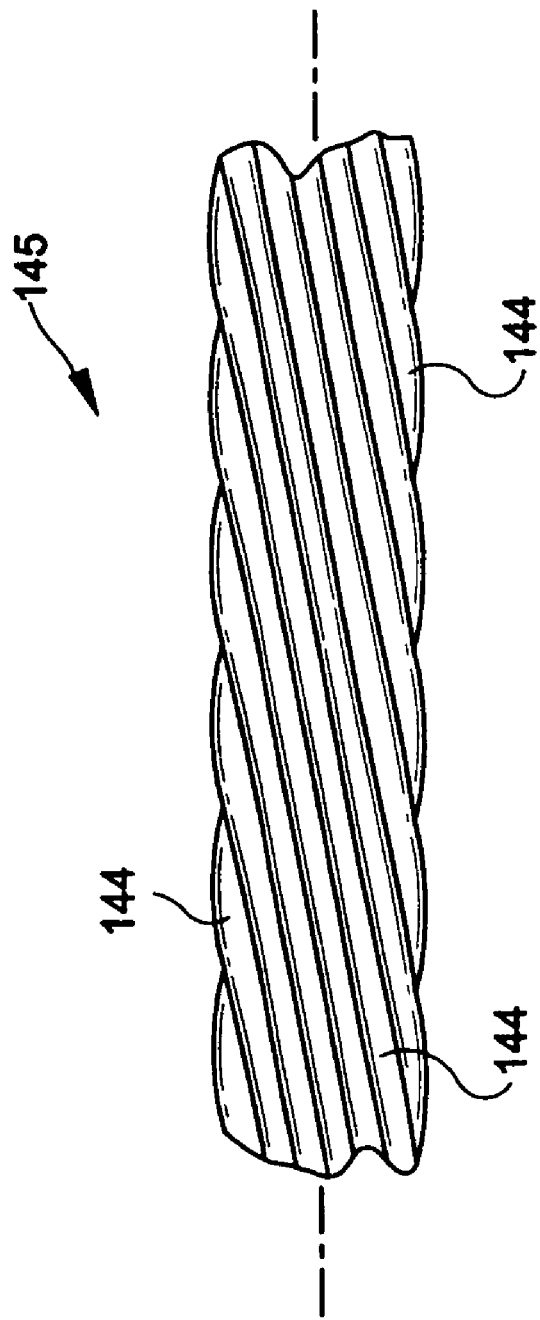
FIG. 13 is a side elevation of a segment of the yarn.

Reference is made to FIG. 11 which shows a cross-section of a monofilament strand 144 which makes up a graft 120. Strands can be woven, braided, or knitted into a tubular fabric shape. FIG. 12 shows a cross-section of a multi-filament yarn 145. FIG. 13 shows the yarn 145 of FIG. 12 in a side elevation with a twist orientation. Additionally, the graft 120 may include extruded or drawn tubes, films, or sheets. The graft 120 may include layers to make a composite structure with optimized porosity and mechanical properties.

Figure 14A:
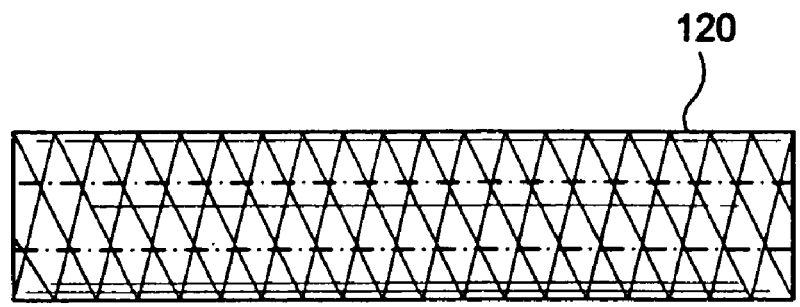
FIGS. 14a-14d are side view of embodiments of permanent grafts.
Figure 14B:
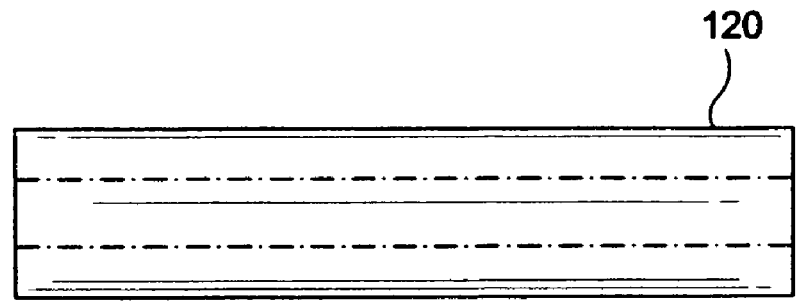
Figure 14C:
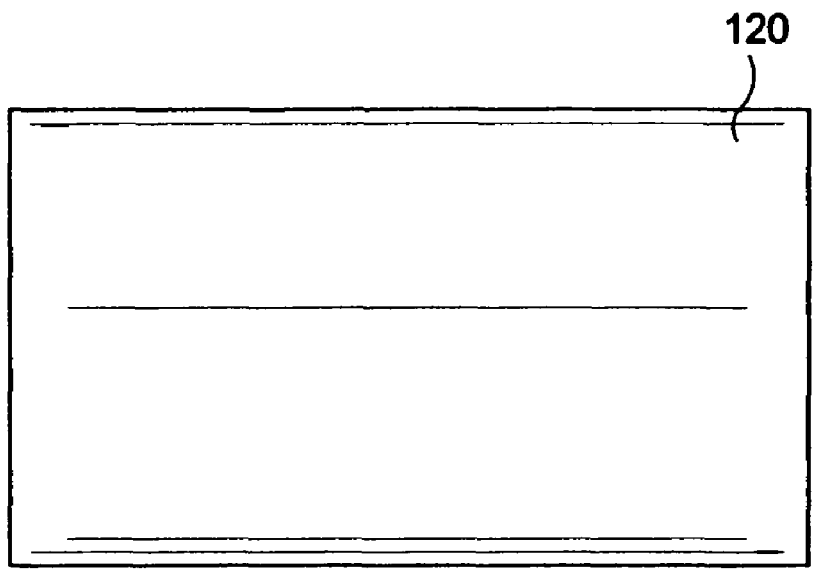
Figure 14D:
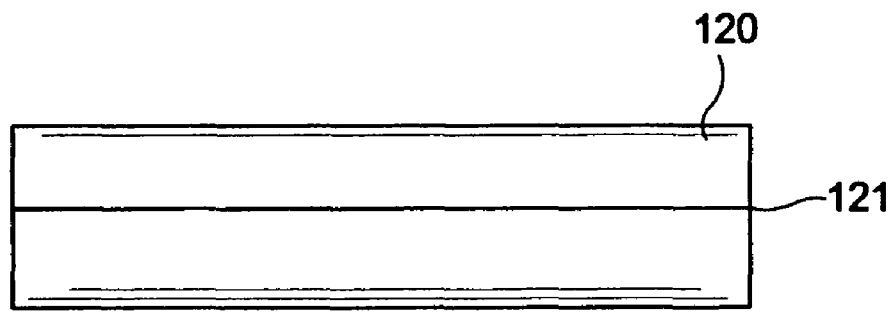

Reference is made to FIGS. 14a-14d showing various embodiments of graft 120. FIG. 14a shows a tubular graft 120, preferably made of PET; FIG. 14b shows a tubular graft 120, preferably made of extruded ePTFE, PCU, or PU; FIG. 14c shows an ePTFE, PCU or PU film or sheet preferably formed in the shape of a tubular graft 120 with a butt joint or overlapping joint 121 as shown in FIG. 14d.

Figure 15:
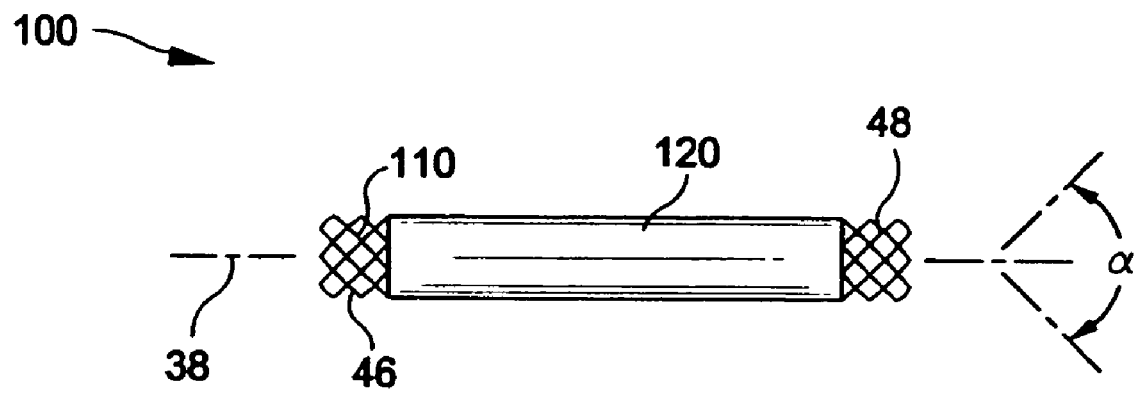
FIG. 15 is a side view of a stent-graft in an unconstrained, radially expanded state.
Figure 16A:
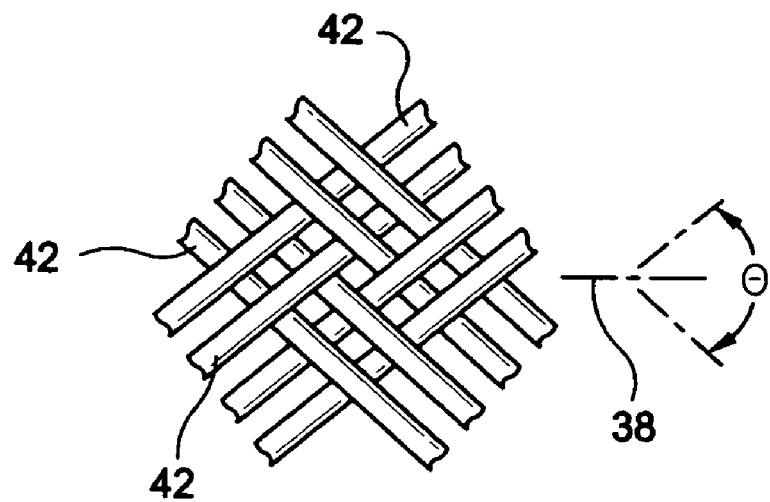
FIGS. 16a-16b are enlarged views of embodiments of grafts, showing the interbraiding of several textile strands.
Figure 16B:
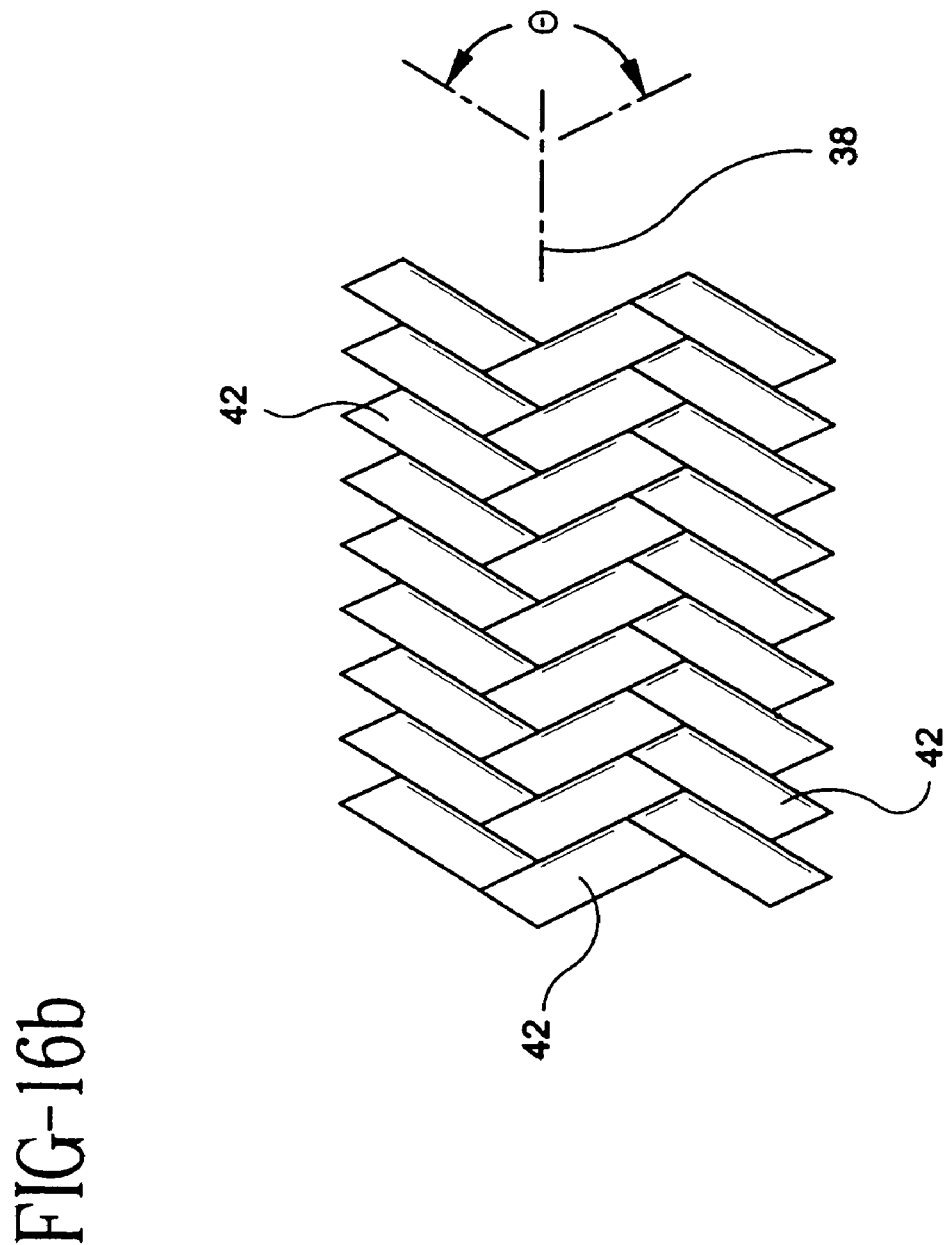

FIG. 15 shows a stent-graft 100 with exposed filament end portions 46 and 48 which are used to facilitate long-term fixation of the stent-graft 100 ends with the vessel wall. FIGS. 16a-b show an exterior layer of stent-graft 100 as a textile sheeting or graft 120, formed of multiple textile strands 42 and interwoven with one another. The textile strands 42 are shown braided in two embodiments in FIGS. 16a and 16b. Other embodiments and patterns may also be used. The textile strands 42 intersect one another to define a braid angle θ in a nominal state. FIGS. 15 and 16 show a filament crossing angle a on stent 110 and a angle θ on graft 120 which bisects a longitudinal axis 38.

Textile strands 42 preferably are multi-filament yarns, although they may be mono-filaments. In either case, the textile strands are finer than the structural strands, and range from about 10 denier to 400 denier. Individual filaments of the multi-filament yarns can range from about 0.25 to about 10 denier.

To form graft 120, the strands or yarns may be interbraided on a mandrel such that they intersect each other and form a braid angle. The number of strands or yarns can range from 20 to 700. The graft 120 is preferably made of PET (Dacron) or polycarbonate urethane (PCU) such as Corethane™, however, other materials may include polypropylene (such as Spectra), polyurethane, HDPE, polyethylene, silicone, PTFE, polyolefins, and ePTFE.

The multi-filament yarns are thermally set in generally the same manner as the bioabsorbable stent 110. After the graft 120 is thermally set, it is removed from the mandrel and washed ultrasonically or by agitation. The graft 120 is then cut to a desired length using a laser, which fuses the ends of the strands to prevent unraveling.

One preferred graft and method of making the same is a braided textile tubular sleeve that is adjustable between a nominal state and a radially-reduced axially-elongated state as described in U.S. patent application entitled "Stent Graft With Braided Polymeric Sleeve", Ser. No. 08/946,906 filed Oct. 8, 1997 (now U.S. Pat. No. 5,957,974) which claims the benefit of U.S. Provisional Application Ser. No. 60/036,160, filed Jan. 23, 1997. A device having a flexible tubular liner is disclosed in U.S. Pat. No. 4,681,110. Several composite braided structures are shown in International Patent Publications Nos. WO 91/10766; WO 92/16166; WO 94/06372; and WO 94/06373. Additional examples are disclosed in U.S. Pat. Nos. 4,475,972; 4,738,740; and 5,653,747. Other examples are disclosed in U.S. patent application Ser. No. 08/640,062 (now U.S. Pat. No. 5,758,562) and U.S. patent application Ser. No 08/640,091 (now U.S. Pat. No. 5,718,159), both filed Apr. 30, 1996 and assigned to the assignee of this application. The graft 120 may be formed of an expandable uniaxially or biaxially oriented polytetrafluoroethylene tube having a microstructure of nodules and fibrils as described in EP 0 775 472 A2.

Table IV illustrates several examples of braided textile fabric grafts having strands with a packing factor of 0.54, and, preferably, a braid angle of about 110 degrees. A coating can be applied to the yarn to enhance surface properties of the yarn and reduce friction.

TABLE IV

| Inner Diameter, mm | # of Yarn Ends | Yarn Linear Density | Fabric Thickness, inch | Yarn Coverage, % | Fabric Porosity, % | Yarn Aspect Ratio |
|---|---|---|---|---|---|---|
| 6 | 72 | 70 | .0031 | 98 | 55 | 6.53 |
| 6 | 96 | 50 | .0032 | 97 | 58 | 4.62 |
| 6 | 120 | 40 | .0034 | 94 | 62 | 3.15 |
| 6 | 144 | 30 | .0032 | 93 | 64 | 2.69 |
| 12 | 192 | 50 | .0032 | 97 | 58 | 4.62 |
| 24 | 352 | 60 | .0035 | 97 | 58 | 4.56 |
| 40 | 512 | 70 | .0034 | 98 | 56 | 5.45 |

Adhesives 130 and methods of manufacturing the stent-graft 100 are discussed in further detail below.

C. Bonding the Graft to the Bioabsorbable Structural Support

A variety of methods and adhesives 130 may be used for bonding the graft 120 to the bioabsorbable structural support 110 are possible. The methods below reference PLLA material, however, other bioabsorbable materials may be used accordingly. A siloxane polymer (silicone) may be used as an adhesive. Other alternative polymers may include fluorosilicone and polycarbonate urethane.

Method 1

A first method includes application of a thermoplastic adhesive to the surface of the PLLA braid by spraying the PLLA braid with a solution of polyurethane or thermoplastic adhesive dissolved in an organic solvent. The graft is disposed over a mandrel and the stent is disposed over the graft. The assembly is heated in an oven at a temperature above the softening temperature of the thermoplastic adhesive and below the melting point of PLLA. The PLLA braid will shrink to the diameter of the mandrel, and make intimate contact with the graft and bond to the graft. The PLLA braid is preferably made such that the braid angle about matches the braid angle of the graft. Adhesives include the polycarbonate urethanes disclosed in U.S. Pat. No. 5,229,431.

Preferred Steps of Method 1

1. Affix the ends of the stent in a fixture which rotates the stent about its central axis.
2. Spray the stent with a 7.5% solids solution of 2.5W30 polycarbonate urethane, such as Corethane™, in DMA. Spray using an airbrush with a 7 cc spray-cup. Spray from a distance of 20-25 centimeters (cm) (8-10 inches) from the stent surface, using a reciprocating motion so as to evenly coat the stent surface.

3. When the spray cup is empty, heat the stent to a temperature above the flashpoint of DMA and below the glass transition temperature of the PLLA. Heat for 5-20 minutes, preferably 10 minutes.
4. Repeat step 2.
5. Repeat step 3.
6. Remove the stent from the fixture and cut off the ends of the stent which were used for gripping and were not sprayed.
7. Place a section of braided PET graft over a mandrel (For example, place 6 mm diameter graft on a 6 mm mandrel).
8. Place the sprayed stent over the mandrel and graft.
9. Affix the ends of the stent to the mandrel, such that the pitch length of the stent matches that of the graft.
10. Place the mandrel/graft/stent in an oven at 120°-165° C. for 5-120 minutes, preferably 165° C. for 20 minutes.

Method 2

A second method includes braiding extruded PLLA filaments to form a tubular interwoven braid and annealing the braid to the desired braid angle and diameter. Apply a thermoplastic adhesive to the surface of the PLLA mesh. Dispose the braid and graft on a mandrel such that, the graft is on the interior and/or exterior of the braid. Apply radial compression or axial elongation to the composite to create intimate contact between the layers. One preferred method of applying radial compression to the structure uses fluorinated ethylene propylene (FEP) "heat-shrink" tubing which reduces in diameter when heated above its glass transition temperature. Bond the composite layers by heating the structure to a temperature above the glass transition temperature of the heat shrink tubing, and below the melting point of the PLLA filaments.

Preferred Steps of Method 2

1. Braid the PLLA mesh.
2. Anneal the mesh to the desired diameter and braid angle by one of the previously described methods.
3. Affix the ends of the stent in a fixture which rotates the stent about its central axis.
4. Spray the stent with a 7.5% solids solution of 2.5W30 polycarbonate urethane, such as Corethane™, in DMA. Spray using an airbrush with a 7 cc spray-cup. Spray from a distance of 20-25 cm (8-10 inches) from the stent surface, using a reciprocating motion so as to evenly coat the stent surface.
5. When the spray-cup is empty, heat the stent to a temperature above the flashpoint of DMA and below the glass transition temperature of the PLLA. Heat for 5-20 minutes, preferably 10 minutes.
6. Repeat step 4.
7. Repeat step 5.
8. Place a graft which has the same braid angle as the stent over or under the stent.
9. Place the stent and graft over a mandrel which matches the ID of the stent, preferably a fluoropolymer-coated stainless steel mandrel.
10. Place a piece of FEP heat shrink tubing over the mandrel and stent/graft so that the heat shrink covers the stent and graft.
11. Heat the assembly in an oven at 120°-165° C. for 5-120 minutes, preferably 165° C. for 20 minutes
12. Remove the heat shrink from the mandrel, and remove the stent-graft from the mandrel.

Method 3

A third method includes braiding extruded PLLA filaments to form a tubular interwoven braid, and anneal the braid to the desired braid angle and diameter. Apply a coating of curable adhesive to the surface of the braid. Disposing the graft on the interior and/or exterior of the braid such that at least a portion of the graft is in contact with the curable adhesive. Heat the composite at a temperature between the cure temperature of the curable adhesive and the glass transition temperature of the PLLA braid.

Preferred Steps of Method 3

1. Braid the PLLA filaments into a braid.
2. Anneal the braid to the desired diameter and braid angle by one of the previously described methods.
3. Affix the ends of the stent in a fixture which rotates the stent about its central axis.
4. Spray the stent with a 6% solids solution of silicone such as Applied Silicone 40,000 in THE and xylene. Spray using an airbrush or atomizer. The spray can be applied either to the ends of the stent or to the total stent length. Apply silicone until the desired thickness is obtained.
5. Apply a stent to the inside and/or outside of the stent so that the graft contacts the silicone adhesive.
6. Place the stent and graft into an oven at 120°-165° C. for 5-120 minutes, preferably 150° C. for 30 minutes.

Method 4

A fourth method includes braiding extruded PLLA filaments to form a tubular interwoven braid, and annealing the braid to the desired braid angle and diameter. Apply a coating of a bioabsorbable polymer "glue" to the surface of the braid by dissolving poly(d-lactide), PDLA in a solvent such as dimethylformamide (DMF), and spray the solution on to the stent. While the polymer "glue" is tacky, place the graft on the interior and/or exterior of the mesh so that all layers of the composite are in contact. Bond the braid to the graft by heating the structure to a temperature above the flash point of the polymer "glue" solvent and below the glass transition temperature of the PLLA braid. This method may also utilize heat shrink as provided in the second method.

Preferred Steps of Method 4

1. Braid the PLLA filaments into a braid.
2. Anneal the braid to the desired diameter and braid angle by one of the previously described methods.
3. Affix the ends of the stent in a fixture which rotates the stent about its central axis.
4. Spray the stent with a 7.5% solids solution of PDLA in DMF. Spray using an airbrush or atomizer. The spray can be applied either to the ends of the stent or to the total stent length. Apply PDLA until the desired thickness is obtained.
5. Apply a stent to the inside and/or outside of the stent so that the graft contacts the silicone adhesive.
6. Place the stent and graft into an oven at 60°-100° C. for 5-120 minutes, preferably 85° C. for 20 minutes.

Method 5

A fifth method includes braiding extruded PLLA filaments to form a tubular interwoven braid, and annealing the braid to the desired braid angle and diameter. Apply a coating of a bioabsorbable polymer "glue" to the surface of the braid.

Placing the graft on the interior and/or exterior of the braid. Bond the braid to the graft by heating the structure to a temperature above the melting point of the polymer "glue" and below the glass transition temperature of the PLLA braid. This method may also utilize heat shrink as provided in the second method.

Preferred Steps of Method 5

1. Braid the PLLA filaments into a braid.
2. Anneal the braid to the desired diameter and braid angle by one of the previously described methods.
3. Affix the ends of the stent in a fixture which rotates the stent about its central axis.
4. Spray the stent with a 7.5% solids solution of PGA in a solvent. Spray using an airbrush with a 7 cc cup. Spray from a distance of 20-25 cm (8-10 inches) from the stent surface, using a reciprocating motion so as to evenly coat the stent surface.
5. When the spray-cup is empty, heat the stent to a temperature above the flashpoint of the solvent and below the glass transition temperature of the PGA. Heat for 5-30 minutes, preferably 10 minutes.
6. Repeat step 4.
7. Repeat step 5.
8. Place a graft which has the same braid angle as the stent over or under the stent.
9. Place the stent and graft over a mandrel which matches the ID of the stent, preferably a fluoropolymer-coated stainless steel mandrel.
10. Place a piece of FEP heat shrink tubing over the mandrel and stent/graft so that the heat shrink covers the stent and graft.
11. Heat the assembly in an oven at 120°-165° C. for 5-120 minutes, preferably 165° C. for 20 minutes.
12. Remove the heat shrink from the mandrel, and remove the stent-graft from the mandrel.

D. Methods of Making a Stent-Graft

Figure 17A:
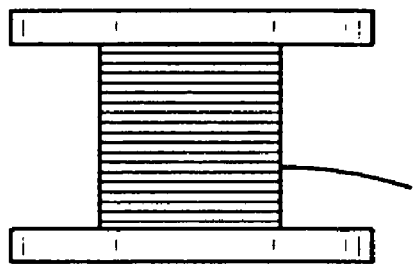
FIGS. 17A-17G schematically illustrate fabrication of a stent-graft.
Figure 17B:
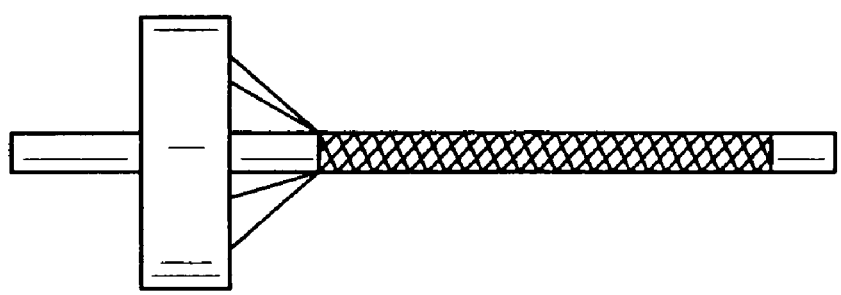
Figure 17C:
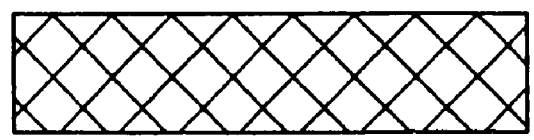
Figure 17D:
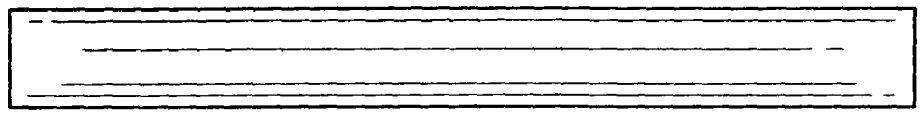
Figure 17E:
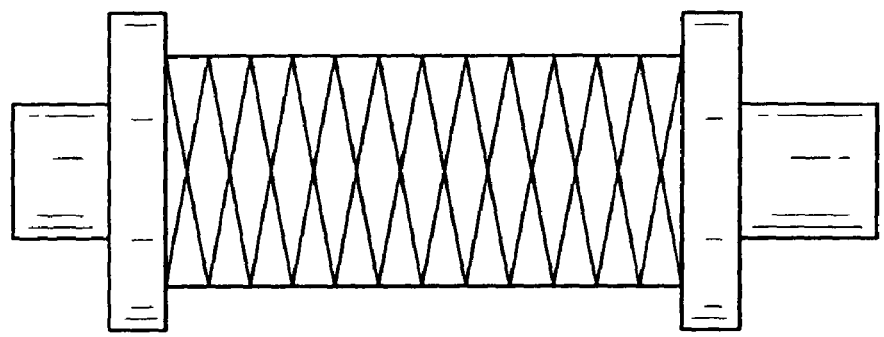
Figure 17F:
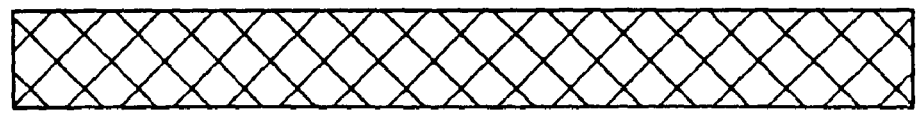
Figure 17G:
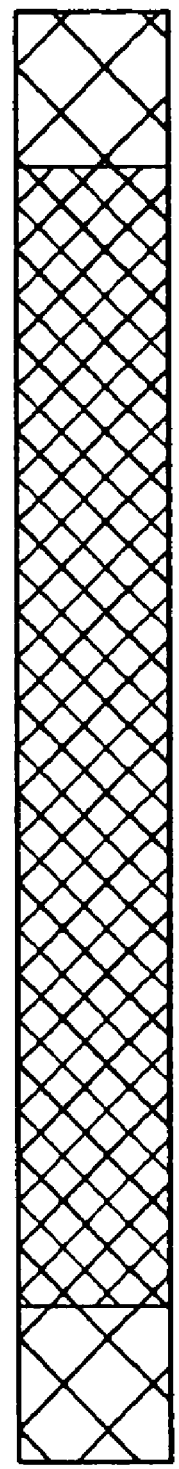

A first method is shown in FIGS. 17A-17G. The steps include providing extruded PLLA filament as shown in FIG. 17A. FIG. 17B shows braiding of extruded filaments to form a tubular interwoven braid. FIG. 17C shows the braid off the mandrel with a braid angle from about 120 to 150 degrees and a diameter of about 11 mm. FIG. 17D shows a straight tubular anneal mandrel, preferably with about a 9 mm diameter. FIG. 17E shows the braid being axially compressed in the anneal mandrel to a diameter of about 11.5 mm. The braid is annealed at a temperature between the glass transition temperature and melting point of the bioabsorbable PLLA filament for 15 minutes in a recirculating air oven. The braid will shrink onto the surface of the mandrel during the annealing cycle. The braid can be designed to shrink to a desired diameter and desired filament crossing angle. FIG. 17F shows the annealed stent off the anneal mandrel with a filament crossing angle from about 130 to 150 degrees. As shown in FIG. 17G, the graft is adhered to the annealed stent using a bioabsorbable adhesive while matching within about plus or minus 5° of the graft braid angle to the annealed stent filament crossing angle.

Figure 18A:
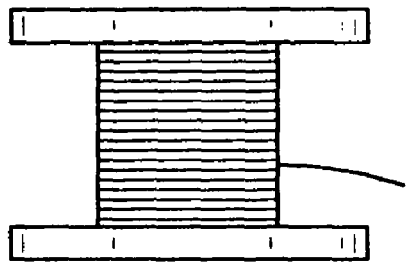
FIGS. 18A-18F schematically illustrate fabrication of a stent-graft.
Figure 18B:
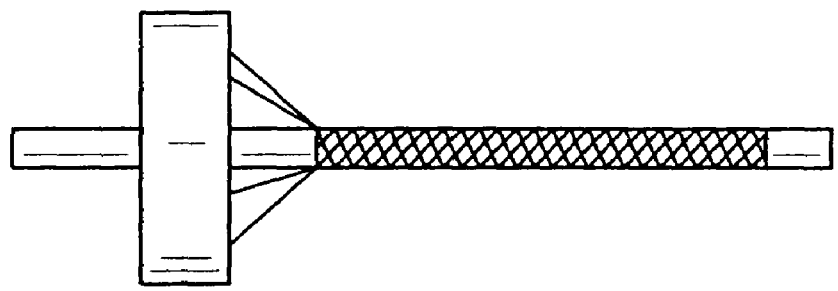
Figure 18C:
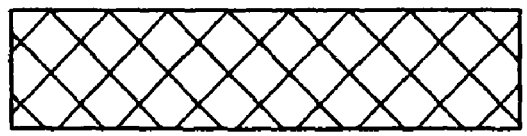
Figure 18D:
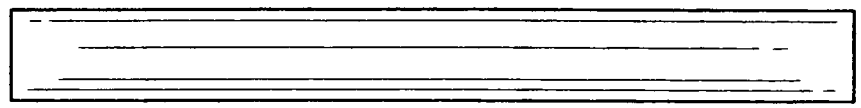
Figure 18E:
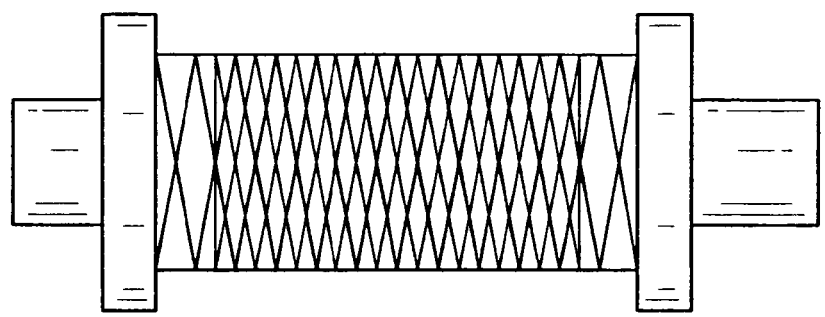
Figure 18F:

A second method is shown in FIGS. 18A-18F. The steps include providing extruded PLLA filament as shown in FIG. 18A. FIG. 18B shows braiding of extruded filaments to form a tubular interwoven braid. FIG. 18C shows the braid off the mandrel with a braid angle from about 120 to 150 degrees and a diameter of about 11 mm. FIG. 18D shows a straight tubular anneal mandrel, preferably with about a 9 mm diameter. FIG. 18E shows the braid and graft being axially compressed in the anneal mandrel to a diameter of about 11.5 mm and being adhered together using a bioabsorbable adhesive while matching within about plus or minus 5° of the graft braid angle to about the braid angle. The braid-graft is annealed at a temperature between the glass transition temperature and melting point of the bioabsorbable PLLA filament for 15 minutes in a recirculating air oven. The braid-graft will shrink onto the surface of the mandrel during the annealing cycle. The braid-graft can be designed to shrink to a desired diameter and filament crossing angle. FIG. 18F shows the annealed stent-graft off the anneal mandrel with a filament crossing angle from about 130 to 150 degrees.

Figure 19A:
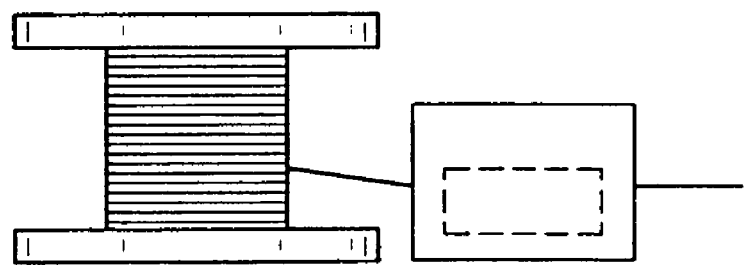
FIGS. 19A-19D schematically illustrate fabrication of a stent-graft.
Figure 19B:
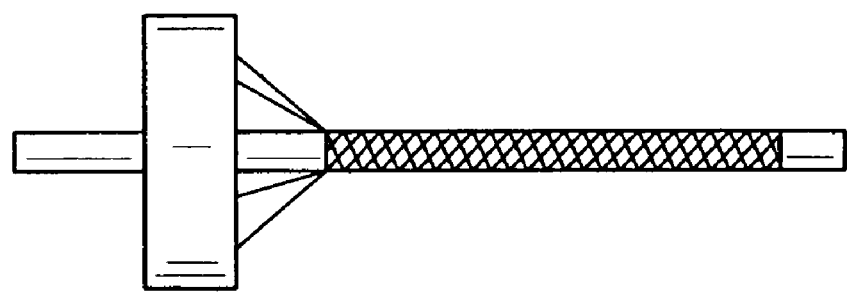
Figure 19C:
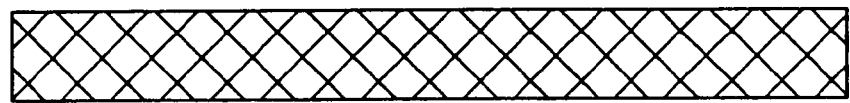
Figure 19D:
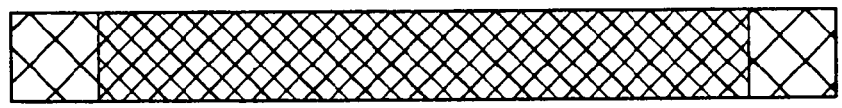

A third method is shown in FIGS. 19A-19D. The steps include providing extruded PLLA filament as shown in FIG. 19A and annealing unconstrained PLLA filaments at a temperature between the glass transition temperature and the melting point for 15 minutes in a recirculating air oven. FIG. 19B shows braiding of extruded annealed filaments to form a tubular interwoven braid. FIG. 19C shows the stent off the mandrel with a filament crossing angle from about 120 to 150 degrees and a diameter of about 10 mm. FIG. 19D shows the stent and graft being adhered together using a bioabsorbable adhesive while matching within about ±5° the graft braid angle to about the filament crossing angle.

Figure 20A:
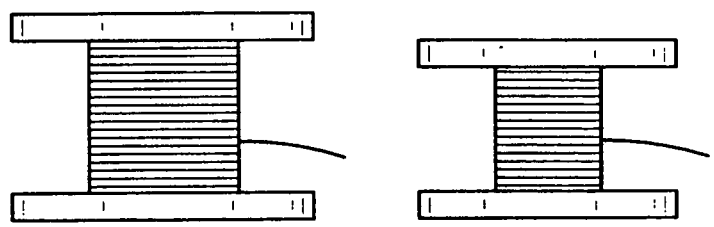
FIGS. 20A-20F schematically illustrate fabrication of a stent-graft.
Figure 20B:
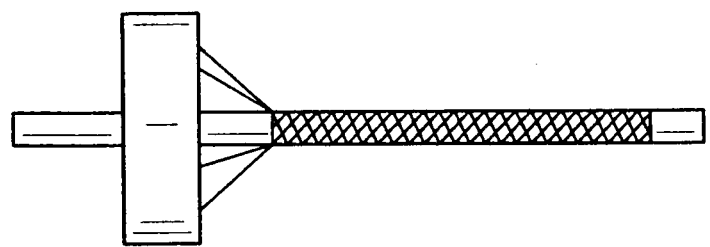
Figure 20C:
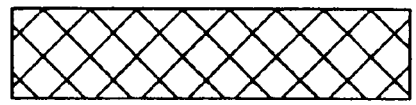
Figure 20D:
Figure 20E:
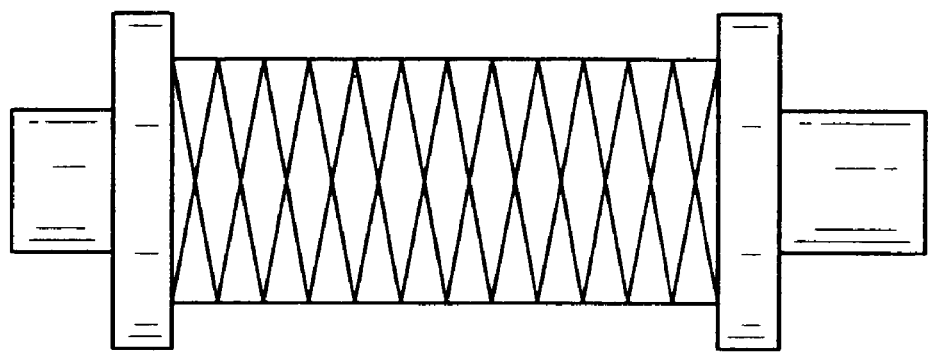
Figure 20F:

A fourth method is shown in FIGS. 20A-20F. The steps include providing extruded PLLA filament and graft fiber as shown in FIG. 20A. FIG. 20B shows co-braiding of extruded filaments and graft to form a tubular interwoven braid-graft. FIG. 20C shows the braid-graft off the mandrel with a braid angle from about 120 to 150 degrees and a diameter of about 11 mm. FIG. 20D shows a straight tubular anneal mandrel, preferably with about a 9 mm diameter. FIG. 20E shows the braid-graft being axially compressed on the anneal mandrel to a diameter of about 11.5 mm. FIG. 20F shows the braid-graft is annealed at a temperature between the glass transition temperature and melting point of the bioabsorbable PLLA filament for 15 minutes in a recirculating air oven. The braid-graft will shrink onto the surface of the mandrel during the annealing cycle. The braid-graft can be designed to shrink to a desired diameter and filament crossing angle. The annealed stent-graft is removed from the anneal mandrel with a filament crossing angle from about 130 to 150 degrees and a diameter of about 10 mm. The interbraiding of PLLA filaments and graft material forms an interwoven tubular mesh with a desired porosity.

E. Stent-Grafts

The graft 120 may surround the outside surface of stent 110 or the stent 110 may surround the outside surface of graft 120. In another embodiment, two grafts 120 may be used to surround and sandwich the stent 110. The filament crossing angle of the assembly generally determines the relationship between radial compression and axial elongation of the stent-graft 100. Smaller angles generally result in less axial shortening for a given amount of radial enlargement. The graft 120 is highly compliant and conforms to changes in the shape of the stent 110.

A primary consideration is to select a braid angle 0 of the graft 120 with respect to a braid angle a of the stent 110, and to closely match the geometrical diameter and elongation properties of the stent 110 and graft 120 formed into the stent-graft 100 by about matching the respective braid angles.

FIG. 21 shows a stent-graft 100 with portions of exposed ends 100A and 100B of the stent 110 coated with adhesive 130. Bond regions 120A and 120B have axial lengths, preferably of about 17 mm, where the stent 110 and graft 120 are coated with adhesive 130 and bonded together. Over a medial region 120C, the graft 120 and stent 110 are adjacent one another and in surface contact, but not bonded.

Figure 22:
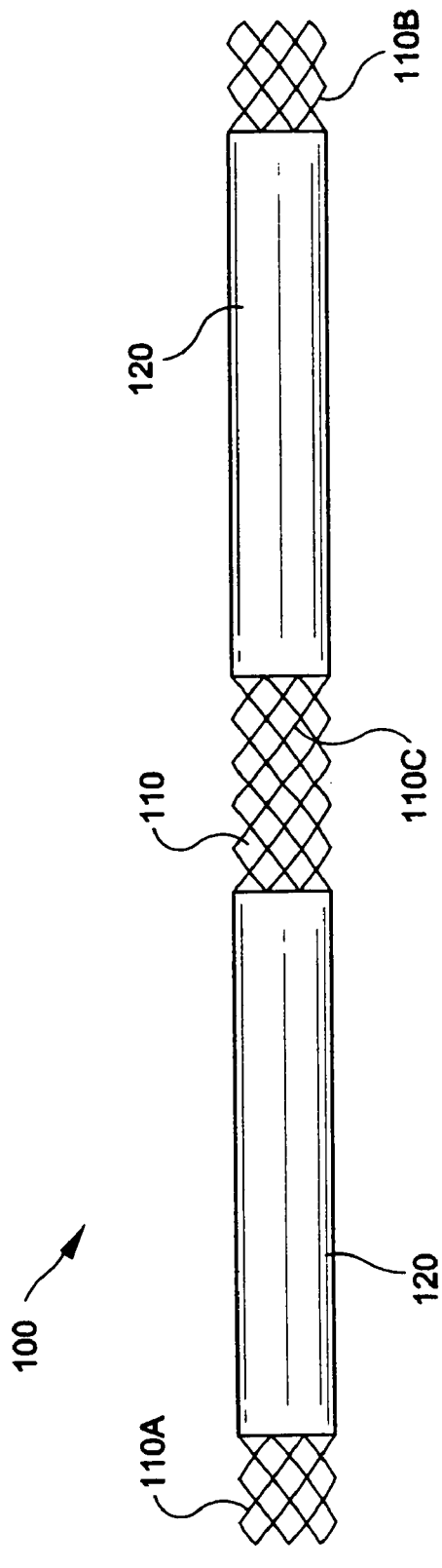
FIG. 22 shows a further alternative stent-graft with selectively positioned grafts.

FIG. 22 shows a stent-graft 100 with a stent 110 surrounded by proximal and distal grafts 120. The stent 110 is exposed at stent-graft end portions 110A, 110B. Each of the grafts 120 is positionable along an intraluminal location where shunting of the blood flow is desired.

An exposed medial region 110C between grafts 120 is positionable in alignment with a branch of the vessel being treated, so that stent-graft 100 can provide the intended shunting without blocking flow between the main vessel and the branch between the two shunting areas.

Figure 23:
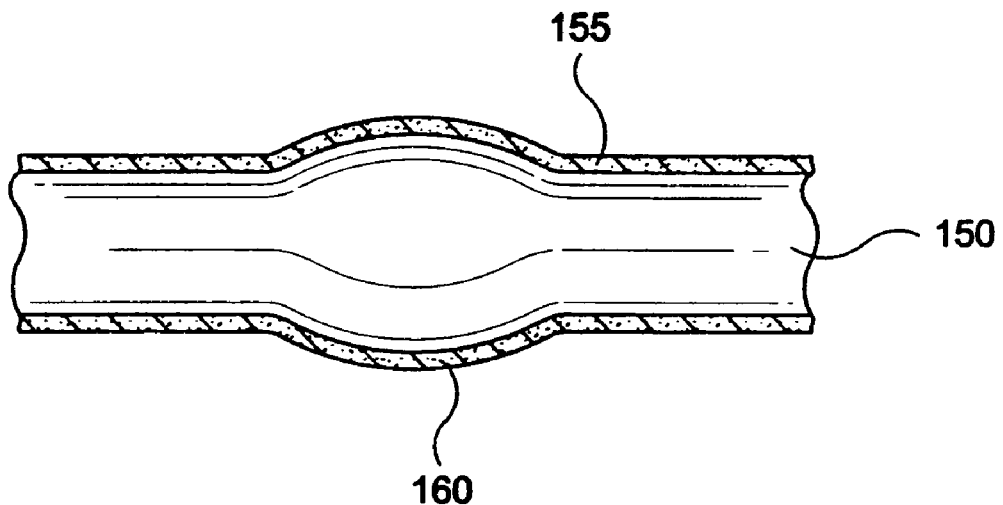
FIGS. 23-26 are side views of the stent-graft function in vivo over time at a treatment site.
Figure 24:
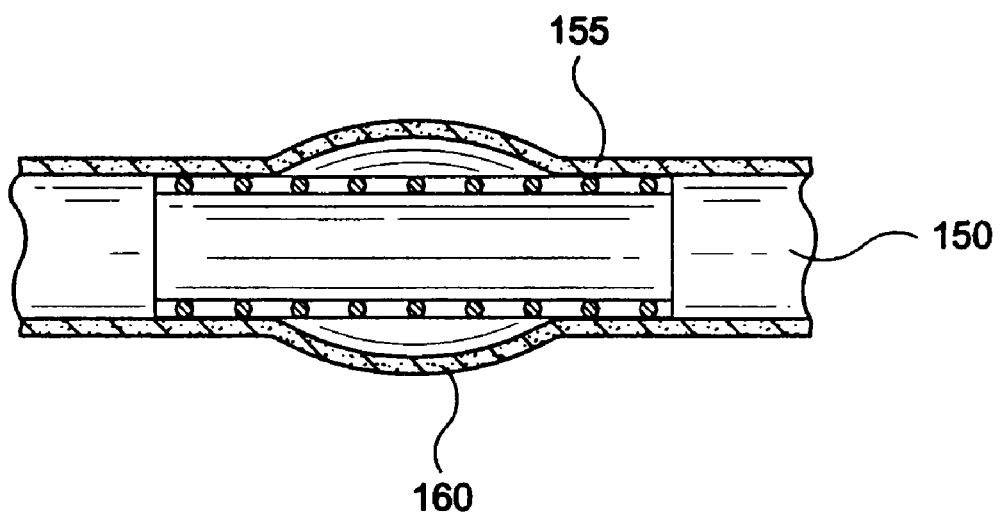
Figure 25:
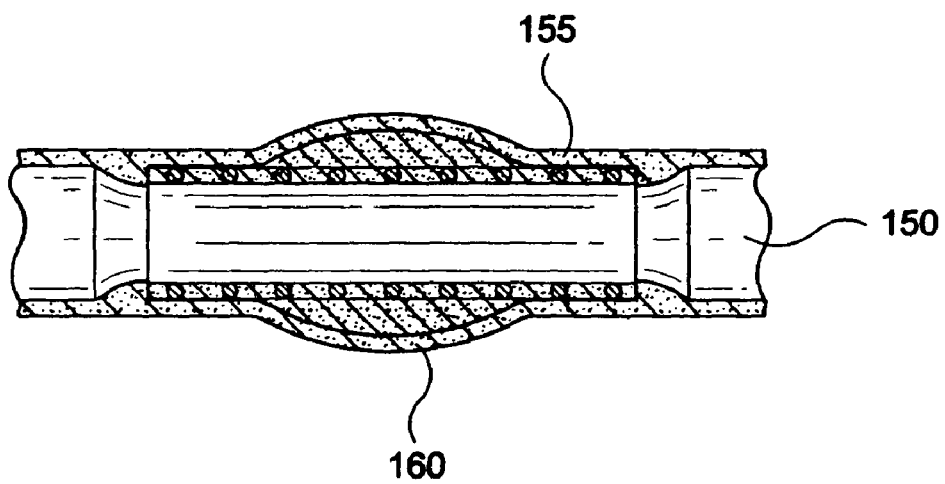
Figure 26:
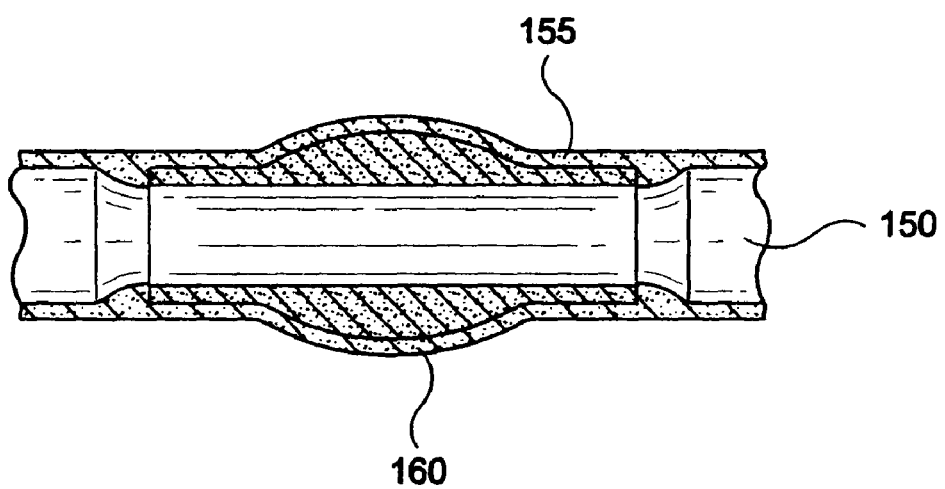

FIG. 23 shows an artery lumen 150, artery wall 155 and an untreated arterial aneurysm 160. FIGS. 24-26 schematically show the stent-graft 100 as it is intended to function in-vivo at a treatment site, for example, an aneurysm. FIG. 24 shows a stent-graft 100 implanted in a artery lumen 150 and within or over an aneurysm 160. FIG. 25 shows healing occurring around the stent-graft 100 with exclusion of the aneurysm 160. FIG. 26 shows the bioabsorbable stent 110 has absorbed and that the graft 120 remains in the artery lumen 150 and has become incorporated in the artery wall 155.

Stent-graft 100 offers considerable advantages. In particular, the polymers from which it is formed are highly biocompatible and exhibit good resistance to thrombosis and bacteria adhesion.

EXAMPLE 1

Stent-graft 100 can be fabricated from a stent 110 having 10 filament strands of 0.15-0.25 mm diameter PLLA, PDLA, PLLA-PDLA copolymer, 0.20-0.30 mm diameter PGA, PGA-PLLA copolymer, 022-0.32 mm diameter PGA-polycaprolactone copolymer, PGA-trimethylcarbonate copolymer, or 0.25-0.35 mm diameter polydioxanone on a 3-6 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 6 French in size.

EXAMPLE 2

Stent-graft 100 can be fabricated from a stent 110 having 10 filament strands of 0.20-0.30 mm diameter PLLA, PDLA, PLLA-PDLA copolymer, 0.25-0.35 mm diameter PGA, PGA-PLLA copolymer, 0.27-0.37 mm diameter PGA-polycaprolactone copolymer, PGA-trimethylcarbonate copolymer, or 0.30-0.40 mm diameter polydioxanone on a 3-6 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 8 French in size.

EXAMPLE 3

Stent-graft 100 can be fabricated from a stent 110 having 12 filament strands of 0.20-0.30 mm diameter PLLA, PDLA, PLLA-PDLA copolymer, 0.25-0.35 mm diameter PGA, PGA-PLLA copolymer, 0.27-0.37 mm diameter PGA-polycaprolactone copolymer, PGA-trimethylcarbonate copolymer, or 0.30-0.40 mm diameter polydioxanone on a 3-8 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 8 French in size.

EXAMPLE 4

Stent-graft 100 can be fabricated from a stent 110 having 12 filament strands of 0.35-0.45 mm diameter PLLA, PDLA, PLLA-PDLA copolymer, 0.40-0.50 mm diameter PGA, PGA-PLLA copolymer, 0.42-0.52 mm diameter PGA-polycaprolactone copolymer, PGA-trimethylcarbonate copolymer, or 0.45-0.55 mm diameter polydioxanone on a 3-8 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 11 French in size.

EXAMPLE 5

Stent-graft 100 can be fabricated from a stent 110 having 16 filament strands of 0.30-0.40 mm diameter PLLA, PDLA, PLLA-PDLA copolymer, 0.35-0.45 mm diameter PGA, PGA-PLLA copolymer, 0.37-0.47 mm diameter PGA-polycaprolactone copolymer, PGA-trimethylcarbonate copolymer, or 0.40-0.50 mm diameter polydioxanone on a 6-10 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 9 French in size.

EXAMPLE 6

Stent-graft 100 can be fabricated from a stent 110 having 16 filament strands of 0.35-0.45 mm diameter PLLA, PDLA, PLLA-PDLA copolymer, 0.40-0.50 mm diameter PGA, PGA-PLLA copolymer, 0.42-0.52 mm diameter PGA-polycaprolactone copolymer, PGA-trimethylcarbonate copolymer, or 0.45-0.55 mm diameter polydioxanone on a 6-10 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 11 French in size.

EXAMPLE 7

Stent-graft 100 can be fabricated from a stent 110 having 18 filament strands of 0.35-0.45 mm diameter PLLA, PDLA, PLLA-PDLA copolymer, 0.40-0.50 mm diameter PGA, PGA-PLLA copolymer, 0.42-0.52 mm diameter PGA-polycaprolactone copolymer, PGA-trimethylcarbonate copolymer, or 0.45-0.55 mm diameter polydioxanone on a 7-12 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 11 French in size.

EXAMPLE 8

Stent-graft 100 can be fabricated from a stent 110 having 18 filament strands of 0.40-0.50 mm diameter PLLA, PDLA, PLLA-PDLA copolymer, 0.45-0.55 mm diameter PGA, PGA-PLLA copolymer, 0.47-0.57 mm diameter PGA-polycaprolactone copolymer, PGA-trimethylcarbonate copolymer, or 0.50-0.60 mm diameter polydioxanone on a 7-12 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 13 French in size.

EXAMPLE 9

Stent-graft 100 can be fabricated from a stent 110 having 20 filament strands of 0.20-0.30 mm diameter PLLA, PDLA, PLLA-PDLA copolymer, 0.25-0.35 mm diameter PGA, PGA-PLLA copolymer, 0.27-0.37 mm diameter PGA-polycaprolactone copolymer, PGA-trimethylcarbonate copolymer, or 0.30-0.40 mm diameter polydioxanone on a 3-9 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 8 French in size.

EXAMPLE 10

Stent-graft 100 can be fabricated from a stent 110 having 24 filament strands of 0.20-0.30 mm diameter PLLA, PDLA, PLLA-PDLA copolymer, 0.25-0.35 mm diameter PGA, PGA-PLLA copolymer, 0.27-0.37 mm diameter PGA-polycaprolactone copolymer, PGA-trimethylcarbonate copolymer, or 0.30-0.40 mm diameter polydioxanone on a 8-12 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 9 French in size.

EXAMPLE 11

Stent-graft 100 can be fabricated from a stent 110 having 24 filament strands of 0.25-0.35 mm diameter PLLA, PDLA, PLLA-PDLA copolymer, 0.30-0.40 mm diameter PGA, PGA-PLLA copolymer, 0.32-0.42 mm diameter PGA-polycaprolactone copolymer, PGA-trimethylcarbonate copolymer, or 0.35-0.45 mm diameter polydioxanone on a 9-14 mm diameter braid mandrel with a filament braid angle of 120-150 degrees while the braid is on the braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 11 French in size.

EXAMPLE 12

Stent-graft 100 can be fabricated from a stent 110 having 24 filament strands of 0.30-0.40 mm diameter PLLA, PDLA, PLLA-PDLA copolymer, 0.35-0.45 mm diameter PGA, PGA-PLLA copolymer, 0.37-0.47 mm diameter PGA-polycaprolactone copolymer, PGA-trimethylcarbonate copolymer, or 0.40-0.50 mm diameter polydioxanone on a 12-18 mm diameter braid mandrel with a filament braid angle of 120-150 degrees while the braid is on me braid mandrel. The braid is annealed on a bar or tube mandrel that has an outer diameter 0.2-3 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 12 French in size.

EXAMPLE 13

Stent-graft 100 can be fabricated from a stent 110 having 30 filament strands of 0.30-0.40 mm diameter PLLA, PDLA, PLLA-PDLA copolymer, 0.35-0.45 mm diameter PGA, PGA-PLLA copolymer, 0.37-0.47 mm diameter PGA-polycaprolactone copolymer, PGA-trimethylcarbonate copolymer, or 0.40-0.50 mm diameter polydioxanone on a 16-26 mm diameter braid mandrel with a filament braid angle of 120-150 degrees while the braid is on the braid mandrel. The braid is annealed on a bar or tube mandrel that has an outer diameter 0.2-6 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 15 French in size.

EXAMPLE 14

Stent-graft 100 can be fabricated from a stent 110 having 36 filament strands of 0.35-0.45 mm diameter PLLA, PDLA, PLLA-PDLA copolymer, 0.40-0.50 mm diameter PGA, PGA-PLLA copolymer, 0.42-0.52 mm diameter PGA-polycaprolactone copolymer, PGA-trimethylcarbonate copolymer, or 0.45-0.55 mm diameter polydioxanone on a 20-30 mm diameter braid mandrel with a filament braid angle of 120-150 degrees while the braid is on the braid mandrel. The braid is annealed on a bar or tube mandrel that has an outer diameter 0.2-6 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 19 French in size.

EXAMPLE 15

Stent-graft 100 can be fabricated from a stent 110 having 24 filament strands of 0.35-0.45 mm diameter PLLA, PDLA, PLLA-PDLA copolymer, 0.40-0.50 mm diameter PGA, PGA-PLLA copolymer, 0.42-0.52 mm diameter PGA-polycaprolactone copolymer, PGA-trimethylcarbonate copolymer, or 0.45-0.55 mm diameter polydioxanone on a 14-20 mm diameter braid mandrel with a filament braid angle of 120-150 degrees while the braid is on the braid mandrel. The braid is annealed on a bar or tube mandrel that has an outer diameter 0.2-6 mm smaller than the braid mandrel diameter at a temperature between the polymer glass-transition temperature and the melting temperature for 5-120 minutes in air, vacuum, or inert atmosphere with the braid in an axially extended, free, or contracted position. The stent is cooled to about room temperature, slid off the anneal mandrel, cut to the desired stent length, and adhered to a graft 120 made of one of PET, ePTFE, PCU, or PU. The stent-graft 100 may be loaded onto a delivery system at least 15 French in size.

| Braid Mandrel Dia., mm | Bioabsorbable Strands in Braid | Bioabsorbable Filament Dia., mm | Bioabsorbable Braid Angle, Deg. | Anneal Mandrel Dia., mm | Annealed Stent I.D., mm | Annealed Stent Filament Crossing Angle, Deg. | Grant Braid mandrel Dia., mm | Strands in Graft Braid | Graft Yarn Denier | Graft Braid Angle, Deg. |
|---|---|---|---|---|---|---|---|---|---|---|
| 8 | 24 | 0.25 | 130-135 | 6 | 6.0 | 105-115 | 6.5 | 120 | 40 | 105-115 |
| 10 | 24 | 0.25 | 130-135 | 7 | 7.0 | 105-115 | 7.5 | 120 | 50 | 105-115 |
| 10 | 24 | 0.25 | 130-135 | 8 | 8.0 | 105-115 | 8.5 | 120 | 50 | 105-115 |
| 12 | 24 | 0.25 | 130-135 | 9 | 9.0 | 105-115 | 9.5 | 120 | 60 | 105-115 |
| 12.5 | 24 | 0.25 | 130-135 | 10 | 10.0 | 105-115 | 10.5 | 192 | 40 | 105-115 |
| 14 | 24 | 0.30 | 130-135 | 12 | 12.0 | 105-115 | 12.5 | 192 | 50 | 105-115 |
| 22 | 36 | 0.35 | 130-135 | 20 | 20.0 | 105-115 | 20.5 | 352 | 40 | 105-115 |
| 25.8 | 36 | 0.40 | 130-135 | 22 | 22.0 | 105-115 | 22.5 | 352 | 50 | 105-115 |
| 28 | 36 | 0.40 | 130-135 | 24 | 24.0 | 105-115 | 24.5 | 352 | 50 | 105-115 |

TABLE VI

| Braid Mandrel Dia., mm | Bioabsorbable Strands in Braid | Bioabsorbable Filament Dia., mm | Bioabsorbable Braid Angle, Deg. | Anneal Mandrel Dia., mm | Annealed Stent I.D., mm | Annealed Stent Filament Crossing Angle, Deg. | Grant Braid mandrel Dia., mm | Strands in Graft Braid | Graft Yarn Denier | Graft Braid Angle, Deg. |
|---|---|---|---|---|---|---|---|---|---|---|
| 8 | 24 | 0.25 | 105-115 | 6 | 6.0 | 105-115 | 6.5 | 120 | 40 | 105-115 |
| 10 | 24 | 0.25 | 105-115 | 7 | 7.0 | 105-115 | 7.5 | 120 | 50 | 105-115 |
| 10 | 24 | 0.25 | 105-115 | 8 | 8.0 | 105-115 | 8.5 | 120 | 50 | 105-115 |
| 12 | 24 | 0.25 | 105-115 | 9 | 9.0 | 105-115 | 9.5 | 120 | 60 | 105-115 |
| 12.5 | 24 | 0.25 | 105-115 | 10 | 10.0 | 105-115 | 10.5 | 192 | 40 | 105-115 |
| 14 | 24 | 0.30 | 105-115 | 12 | 12.0 | 105-115 | 12.5 | 192 | 50 | 105-115 |

TABLE VI-continued

| Braid Mandrel Dia., mm | Bioabsorbable Strands in Braid | Bioabsorbable Filament Dia., mm | Bioabsorbable Braid Angle, Deg. | Anneal Mandrel Dia., mm | Annealed Stent I.D., mm | Annealed Stent Filament Crossing Angle, Deg. | Graft Braid mandrel Dia., mm | Strands in Graft Braid | Graft Yarn Denier | Graft Braid Angle, Deg. |
|---|---|---|---|---|---|---|---|---|---|---|
| 22 | 36 | 0.35 | 105-115 | 20 | 20.0 | 105-115 | 20.5 | 352 | 40 | 105-115 |
| 25.8 | 36 | 0.40 | 105-115 | 22 | 22.0 | 105-115 | 22.5 | 352 | 50 | 105-115 |
| 28 | 36 | 0.40 | 105-115 | 24 | 24.0 | 105-115 | 24.5 | 352 | 50 | 105-115 |

TABLE VII

| Braid Mandrel Dis., mm | Bioabsorbable Strands in Braid | Bioabsorbable Filament Dia., mm | Bioabsorbable Braid Angle, Degrees | Graft Braid Mandrel Dia., mm | Strands in Graft Braid | Graft Yarn Denier | Graft Braid Angle, Degrees |
|---|---|---|---|---|---|---|---|
| 6 | 24 | 0.25 | 105-115 | 6.5 | 120 | 40 | 105-115 |
| 7 | 24 | 0.25 | 105-115 | 7.5 | 120 | 50 | 105-115 |
| 8 | 24 | 0.25 | 105-115 | 8.5 | 120 | 50 | 105-115 |
| 9 | 24 | 0.25 | 105-115 | 9.5 | 120 | 60 | 105-115 |
| 10 | 24 | 0.25 | 105-115 | 10.5 | 192 | 40 | 105-115 |
| 12 | 24 | 0.30 | 105-115 | 12.5 | 192 | 50 | 105-115 |
| 20 | 36 | 0.35 | 105-115 | 20.5 | 352 | 40 | 105-115 |
| 22 | 36 | 0.40 | 105-115 | 22.5 | 352 | 50 | 105-115 |
| 24 | 36 | 0.40 | 105-115 | 24.5 | 352 | 50 | 105-115 |

TABLE VIII

| Braid Mandrel Dia., mm | Bioabsorbable Strands in Braid | Bioabsorbable Filament Dia., mm | Bioabsorbable Braid Angle, Deg. | Graft Yarn Denier | Graft Braid Angle, Deg. | Anneal Mandrel Dia., mm | Annealed Stent I.D., mm | Annealed Stent Filament Crossing Angle, Deg. | Graft Braid Angle, Deg. |
|---|---|---|---|---|---|---|---|---|---|
| 8 | 24 | 0.25 | 130-135 | 40 | 130-135 | 6 | 6.0 | 105-115 | 105-115 |
| 10 | 24 | 0.25 | 130-135 | 50 | 130-135 | 7 | 7.0 | 105-115 | 105-115 |
| 10 | 24 | 0.25 | 130-135 | 50 | 130-135 | 8 | 8.0 | 105-115 | 105-115 |
| 12 | 24 | 0.25 | 130-135 | 60 | 130-135 | 9 | 9.0 | 105-115 | 105-115 |
| 12.5 | 24 | 0.25 | 130-135 | 40 | 130-135 | 10 | 10.0 | 105-115 | 105-115 |
| 14 | 24 | 0.30 | 130-135 | 50 | 130-135 | 12 | 12.0 | 105-115 | 105-115 |
| 22 | 36 | 0.35 | 130-135 | 40 | 130-135 | 20 | 20.0 | 105-115 | 105-115 |
| 25.8 | 36 | 0.40 | 130-135 | 40 | 130-135 | 22 | 22.0 | 105-115 | 105-115 |
| 28 | 36 | 0.40 | 130-135 | 50 | 130-135 | 24 | 24.0 | 105-115 | 105-115 |

Another embodiment of the stent-graft 100 includes at least one bioabsorbable-radiopaque marker strand disposed thereon to visualize the position of the stent-graft 100 through fluoroscopy during implantation.

Bioabsorbable markers that may advantageously be used in conjunction with the present invention are disclosed in U.S. patent applications entitled "Radiopaque Markers And Methods Of Using Same", Ser. No. 08/905,821 (now U.S. Pat. No. 6,340,367) and "Bioabsorbable Marker Having Radiopaque Constituents And Method Of Using Same", Ser. No. 08/904,951 (now U.S. Pat. No. 6,174,330) both filed Aug. 1, 1997.

Figure 27:
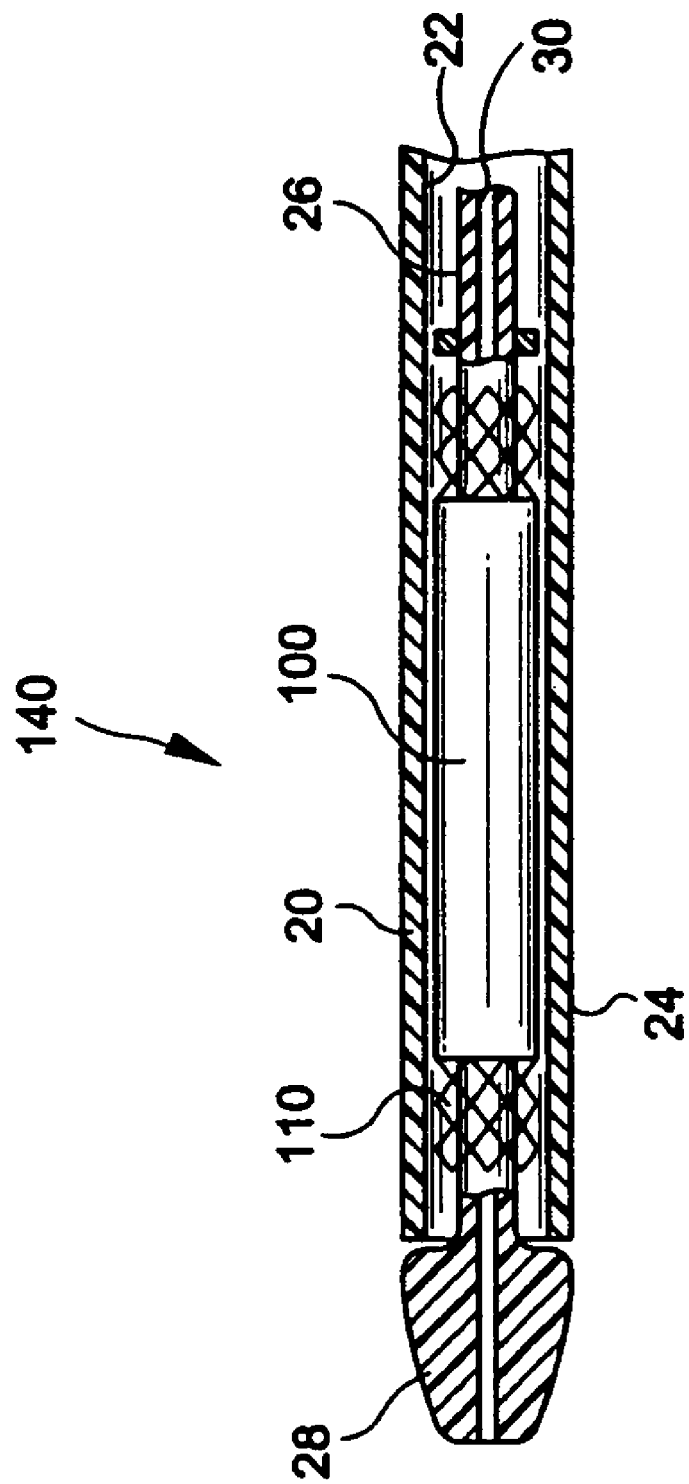
FIG. 27 is a side elevation, partially in, section, showing a stent-graft contained within a deployment device.

A delivery device is used for delivering the stent-graft 100 to a treatment site in a body vessel. Reference is made to FIG. 27 showing a delivery device 140 for delivering a stent-graft 100 to a treatment site within a body lumen which is used to controllably release the stent-graft 100 within the lumen. The delivery device 140 generally includes an elongate and flexible outer catheter 20 constructed of a biocompatible polymer such as polyurethane. A central lumen 22 runs the length of catheter 20. A distal end region 24 of the outer catheter surrounds stent-graft 100. An inner catheter 26 is contained within lumen 22 and runs along the entire length of the outer catheter. At the distal end of inner catheter 26 is a tapered distal tip 28 which extends beyond the outer catheter. Stent-graft 100 surrounds inner catheter 26, confined between the inner and outer catheters. A lumen 30 in the inner catheter can accommodate a flexible guidewire (not shown) tracked by delivery device 140 as it is advanced toward the treatment site.

Stent-graft 100 may be placed on the delivery device 140 in a radially compressed state. Preferred delivery devices are shown in U.S. Pat. Nos. 4,954,126 and 5,026,377. Alternative delivery devices are shown in U.S. Pat. Nos. 5,201,757; 5,484,444; 5,591,172; 5,628,755; and 5,662,703. Suitable materials for use with such delivery devices are described in U.S. patent application Ser. No. 08/833,639, filed Apr. 8, 1997 (now U.S. Pat. No. 6,042,578).

A pusher-type delivery system provides generally greater self-expansion of the stent-graft 100 than a coaxial inner-outer tube-type delivery system. Pushing the proximal end of the stent-graft 100 out the distal end of the delivery system results in more self expansion than when the stent is released by sliding back the outer tube of the catheter delivery system.

The preferred delivery system size for stent-graft 100 is the external diameter in French size of about 7-20 French (French size is equivalent to about three times the diameter in mm).

Figure 28:
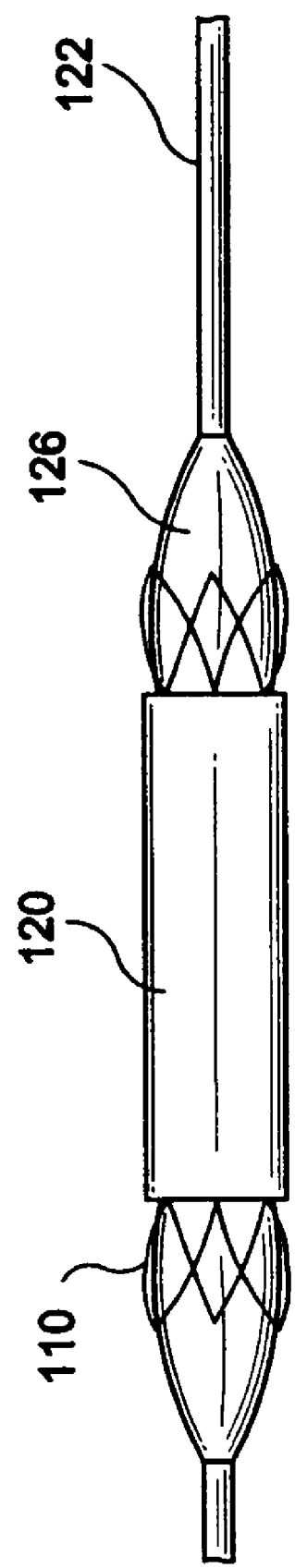
FIG. 28 illustrates a stent-graft mounted on an alternative deployment device.

An alternative delivery device is shown in FIG. 28 where a distal end region of a catheter 122 is used to deploy the stent-graft 100. Stent-graft 100 is designed to remain in the axially elongated, radially reduced delivery state as shown, without additional constraining features. An auxiliary forcing feature is required to urge the stent-graft 100, once properly positioned at a treatment site, toward its normal state. For this purpose a dilatation balloon 126 is mounted to catheter 122 and surrounded by the stent-graft 100. The balloon 126, when inflated by the introduction of fluid under pressure through a lumen in catheter 122, radially expands the stent-graft 100.

Although the present invention has been described with reference to preferred embodiments, those skilled in the art will recognize that changes can be made in form and detail without departing from the spirit and scope of the invention.

It will be evident from considerations of the foregoing that the bioabsorbable self-expanding stent-graft 100 may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

The invention claimed is:

1. A method of using a stent-graft comprising:
providing a stent-graft assembly, said stent-graft assembly formed by the method comprising the steps of: disposing a tubular body comprising bioabsorbable material on a mandrel; disposing a compliant and substantially non-absorbable graft layer on the mandrel such that one of the tubular body and the graft layer surrounds the other over at least a coextensive portion; and with the tubular body and the graft layer so disposed, adhering the graft layer to the tubular body with a bioabsorbable adhesive to form a stent-graft in which the tubular body is radially expandable and contractible and the graft layer tends to conform to the tubular body as the tubular body radially expands and contracts;
deploying the stent-graft assembly into a body lumen at a treatment site; and
allowing the stent-graft assembly to self-expand or expanding the stent-graft assembly in the body lumen.

2. The method of claim 1, wherein said tubular body is formed by helically winding a plurality of bioabsorbable filaments.

3. The method of claim 2, wherein said tubular body is annealed at a temperature between a glass transition temperature of the bioabsorbable filaments and a melting point of the bioabsorbable filaments.

4. The method of claim 3, wherein said annealing of the tubular body is performed after said adhering the graft layer to the tubular body.

5. The method of claim 2, wherein said forming the bioabsorbable tubular body includes interbraiding the filaments.

6. The method of claim 1, wherein said disposing the graft layer on the mandrel includes surrounding the tubular body with the graft layer.

7. The method of claim 1, wherein said disposing the graft layer on the mandrel includes surrounding the graft layer with the tubular body.

8. The method of claim 1, wherein said adhering the graft layer to the tubular body comprises applying an adhesive only to proximal and distal end portions of the coextensive portion.

* * * * *